US008120760B2

(12) United States Patent
Stanton et al.

(10) Patent No.: US 8,120,760 B2
(45) Date of Patent: Feb. 21, 2012

(54) METHOD AND APPARATUS FOR SEPARATING A COMPOSITE LIQUID INTO AT LEAST TWO COMPONENTS AND FOR DETERMINING THE YIELD OF AT LEAST ONE COMPONENT

(75) Inventors: Briden Ray Stanton, Highlands Ranch, CO (US); Geert Van Waeg, Brussels (BE)

(73) Assignee: CaridianBCT, Inc., Lakewood, CO (US)

( * ) Notice: Subject to any disclaimer, the term of this patent is extended or adjusted under 35 U.S.C. 154(b) by 407 days.

(21) Appl. No.: 12/494,476

(22) Filed: Jun. 30, 2009

(65) Prior Publication Data
US 2010/0026986 A1 Feb. 4, 2010

Related U.S. Application Data

(60) Provisional application No. 61/085,236, filed on Jul. 31, 2008, provisional application No. 61/154,096, filed on Feb. 20, 2009.

(51) Int. Cl.
*G01N 33/48* (2006.01)
(52) U.S. Cl. .......................................... 356/39
(58) Field of Classification Search ...................... 356/39
See application file for complete search history.

(56) References Cited

U.S. PATENT DOCUMENTS

| 3,297,244 A | 1/1967 | Hein |
| 3,326,458 A | 6/1967 | Meryman et al. |
| 3,679,128 A | 7/1972 | Unger et al. |
| 3,708,110 A | 1/1973 | Unger et al. |
| 3,724,747 A | 4/1973 | Unger et al. |
| 3,737,096 A | 6/1973 | Jones et al. |
| 3,858,796 A | 1/1975 | Unger et al. |
| 3,987,961 A | 10/1976 | Sinn et al. |
| 4,146,172 A | 3/1979 | Cullis et al. |
| 4,389,207 A | 6/1983 | Bacehowski et al. |
| 4,405,079 A | 9/1983 | Schoendorfer |
| 4,421,503 A | 12/1983 | Latham, Jr. et al. |
| 4,482,342 A | 11/1984 | Lueptow et al. |
| 4,720,284 A | 1/1988 | McCarty |
| 4,850,995 A | 7/1989 | Tie et al. |
| 4,990,132 A | 2/1991 | Unger et al. |
| 5,114,396 A | 5/1992 | Unger et al. |
| 5,427,695 A | 6/1995 | Brown |

(Continued)

FOREIGN PATENT DOCUMENTS

EP 0499891 8/1992

(Continued)

OTHER PUBLICATIONS

International Search Report for Corresponding Application PCT/US2009/049140, mailed Feb. 11, 2010.

*Primary Examiner* — Roy M Punnoose
(74) *Attorney, Agent, or Firm* — Edna M. O'Connor; John R. Herkling; Laura B Arciniegas

(57) ABSTRACT

Method and Apparatus for predicting the yield of a selected cellular component from a composite blood product by sensing the movement of the separated cellular component or another component during expression from a separation container to a collection container to produce a signal indicative of the movement, and predicting the yield of the separated cellular component from the signal.

34 Claims, 12 Drawing Sheets

U.S. PATENT DOCUMENTS

| | | | |
|---|---|---|---|
| 5,543,062 A | 8/1996 | Nishimura | |
| 5,632,906 A | 5/1997 | Ishida et al. | |
| 5,723,050 A | 3/1998 | Unger et al. | |
| 5,738,644 A | 4/1998 | Holmes et al. | |
| 5,874,208 A | 2/1999 | Unger | |
| 5,904,355 A | 5/1999 | Powers et al. | |
| 5,964,724 A | 10/1999 | Rivera et al. | |
| 6,261,217 B1 | 7/2001 | Unger et al. | |
| 6,296,602 B1 | 10/2001 | Headley | |
| 6,315,706 B1 | 11/2001 | Unger et al. | |
| 6,348,031 B1 | 2/2002 | Unger et al. | |
| 6,439,577 B2 | 8/2002 | Jorgensen et al. | |
| 6,605,223 B2 | 8/2003 | Jorgensen et al. | |
| 6,656,105 B2 | 12/2003 | Hogberg et al. | |
| 6,740,239 B2 | 5/2004 | Hogberg et al. | |
| 7,033,512 B2 | 4/2006 | Hlavinka et al. | |
| 7,166,217 B2 | 1/2007 | Holmes et al. | |
| 7,279,107 B2 | 10/2007 | Hogberg et al. | |
| 7,347,932 B2 | 3/2008 | Holmes et al. | |
| 7,396,451 B2 | 7/2008 | Holmes et al. | |
| 7,413,665 B2 | 8/2008 | Holmes et al. | |
| 7,463,343 B2 * | 12/2008 | Muller | 356/39 |
| 2002/0014462 A1 * | 2/2002 | Muller | 210/745 |
| 2002/0119880 A1 | 8/2002 | Hogberg et al. | |
| 2004/0026341 A1 | 2/2004 | Hogberg et al. | |
| 2007/0179423 A1 | 8/2007 | Felt et al. | |
| 2007/0203444 A1 | 8/2007 | Felt et al. | |
| 2007/0209708 A1 | 9/2007 | Hermann et al. | |
| 2007/0284320 A1 | 12/2007 | Menhennett et al. | |
| 2008/0009833 A1 | 1/2008 | Corbin et al. | |
| 2008/0053203 A1 | 3/2008 | Hogberg et al. | |
| 2008/0087613 A1 | 4/2008 | Hudock et al. | |
| 2008/0090714 A1 | 4/2008 | Hudock et al. | |
| 2008/0147240 A1 | 6/2008 | Hudock et al. | |
| 2008/0149564 A1 | 6/2008 | Holmes | |
| 2008/0220959 A1 | 9/2008 | Holmes et al. | |
| 2008/0283473 A1 | 11/2008 | Holmes et al. | |
| 2008/0314822 A1 | 12/2008 | Holmes et al. | |

FOREIGN PATENT DOCUMENTS

| | | |
|---|---|---|
| EP | 0771569 | 5/1997 |
| EP | 1566191 | 8/2005 |
| EP | 1757318 | 2/2007 |
| WO | WO92/00145 | 1/1992 |
| WO | WO01/02037 | 1/2001 |
| WO | WO01/97943 | 12/2001 |
| WO | WO03/089027 | 10/2003 |
| WO | WO2004/018021 | 3/2004 |
| WO | WO2005/082540 | 9/2005 |
| WO | WO2006/071496 | 7/2006 |

* cited by examiner

METHOD AND APPARATUS FOR SEPARATING A COMPOSITE LIQUID INTO AT LEAST TWO COMPONENTS AND FOR DETERMINING THE YIELD OF AT LEAST ONE COMPONENT

FIELD OF THE INVENTION

The present invention concerns a method and apparatus for separating a volume of composite liquid or blood product into at least two components and for predicting the yield of at least one of the components. The invention also relates to a method for selecting buffy coat or random donor platelet collections to produce a more consistent or desirable platelet product for transfusion. The method can also help determine any buffy coat or random donor platelet collections to be discarded and can be used to optimize the collection of one component as compared to another component.

BACKGROUND

The method and apparatus of the invention is appropriate for the separation of biological fluids comprising an aqueous component and are one or more cellular components. For example, potential uses of the invention include extracting, from a volume of whole blood, a plasma component and, a first cellular component including platelets. The first cellular component alternatively may be a buffy coat component. The invention is also useful when the pooling of buffy coat or random donor platelet collections occurs for a platelet product.

European patent application EP 1566191 describes a method and an apparatus for separating a volume of whole blood into at least two components in accordance with various separation protocols. For example, one protocol provides for the separation of a volume of whole blood into a plasma component, a platelet component, and a red blood cell component. The apparatus comprises a centrifuge adapted to cooperate with various bag sets, in particular a bag set comprising an annular separation bag for whole blood, which is connected to a platelet component bag, a plasma component bag, and a red blood cell component bag. The centrifuge includes a rotor for spinning the separation bag and centrifuging the whole blood contained therein, the rotor having a turntable for supporting the separation bag and a central compartment for containing the component bags connected to the separation bag; and a squeezing system for squeezing the separation bag and causing the transfer of the plasma component from the separation bag into the plasma component bag, and of the platelet component into the platelet component bag. When such a platelet product is collected it is frequently desirable to know or predict the yield of the collected product. This can be important for subsequent use of the platelet product for transfusion and when such platelet product is pooled with other collections to form a random donor platelet product.

U.S. patent application Ser. No. 11/954388 filed Dec. 12, 2007 further describes a alternate method of separating at least two discrete volumes of a composite liquid into at least two components.

Buffy coat produced from a whole blood donation is a combination of platelets and white blood cells with a small amount of red blood cells and plasma. The majority of platelets collected during a whole blood donation are in the buffy coat layer. WO 2004/018021 describes a process of separating buffy coats as well as platelets from a composite blood product. To produce a platelet dosage amount, buffy coats are pooled from many donations and re-spun in a centrifuge to separate the platelets from the rest of the buffy coat.

These pooled buffy coat platelets form the dosage of platelet product. One pooled platelet product can include buffy coat platelets from a number of collections. It is desirable that this pooled platelet product also form a consistent dose. U.S. Pat. No. 6,348,031 discloses an apparatus for pooling buffy coats to achieve a platelet dosage product.

It is against this background of the desire for a consistent and pure platelet dose product that the instant invention was conceived and developed.

SUMMARY OF THE INVENTION

One object of the instant invention is to provide a method for producing a predictable platelet dosage for therapeutic purposes.

An additional object of the invention is to provide a method and apparatus to predict the yield of platelets in a buffy coat collection or in a platelet collection.

Another object of the invention is to provide a method to select several buffy coat or random donor platelet collections to achieve a predictable platelet dosage.

The method of the instant invention includes predicting the yield of a selected cellular component, such as platelets, from a composite blood product by centrifuging the blood product to separate the cellular component; expressing the cellular component to a collection container; sensing the movement of the separated cellular component to the collection container by a sensor such as a photocell to produce a signal indicative of the movement; and predicting the yield of the separated cellular component from the signal.

The method can further include changing the collection procedure or separation protocol in favor of another component collection to avoid collecting a platelet product unsuitable for pooling while optimizing the collection of another component.

Also provided is a method of selecting buffy coat or random donor platelet collections to achieve a desired platelet product. The method includes predicting the platelet yield in a plurality of collected buffy coat or random donor platelet collections; selecting the desired buffy coat or random donor platelet collections to achieve the desired end platelet product; combining selected buffy coat or random donor platelet collections to achieve the desired yield of platelets in the platelet dosage amount.

Also provided is apparatus including a separation container, a collection container, a centrifuge for centrifuging the composite blood product in the separation container to separate the composite blood product into at least the one selected cellular component, a system for expressing the separated cellular component from the separation container to the at least one collection container, a sensor for sensing the movement of the separated cellular component during expression from the separation container to the collection container to produce a signal indicative of the cellular component movement, and a controller for predicting the yield of the separated cellular component from the signal.

BRIEF DESCRIPTION OF THE DRAWINGS

In the accompanying drawings.

DESCRIPTION OF THE EMBODIMENTS

For the sake of clarity, the invention will be described with respect to a specific use, including the separation of whole blood into three components, namely a plasma component, a platelet or buffy coat component, and a red blood cell component. It should be understood however that this specific use is exemplary only. It should also be understood that the principles can be used for collecting at least two components or even four components.

Figure 1:
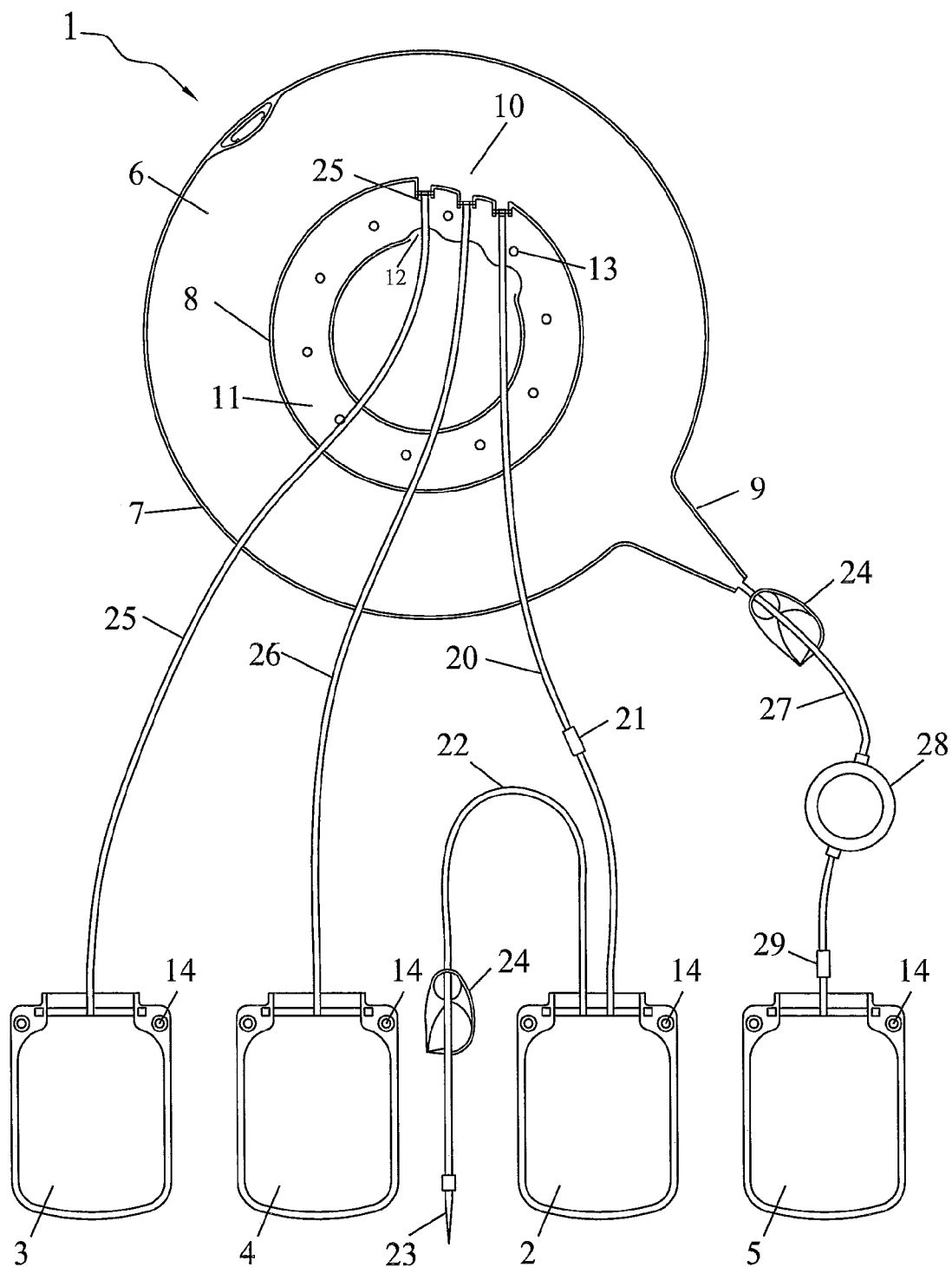
FIG. 1 is a schematic view of a set of bags designed for cooperating with a separation apparatus according to the invention.
Figure 2:
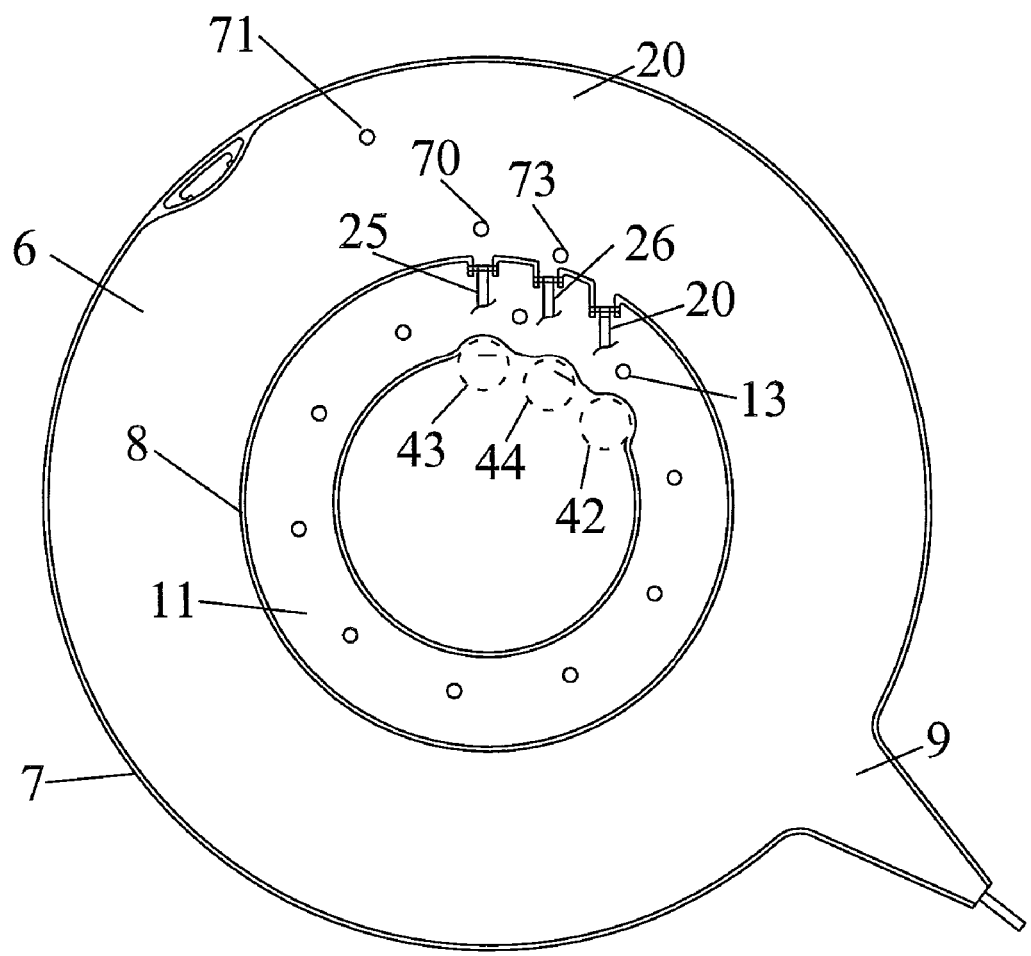
FIG. 2 is an enlarged view of the separation bag of the set of bags of FIG. 1.

FIGS. 1 and 2 show an example of a set of bags adapted to the separation of whole blood or a composite blood product into a plasma component (essentially comprising plasma), a platelet component (essentially comprising platelets), and a red blood cell component (essentially comprising red blood cells). As described latter the platelet component can also be a buffy coat component. This bag set comprises a flexible separation bag or container 1 and four flexible satellite bags or product or collection containers 2, 3, 4, 5 connected thereto. The separation bag 1 comprises an annular separation chamber 6 having generally circular outer and inner edges 7, 8. The outer circular edge 7 and the inner circular edge 8 of separation chamber 6 are substantially concentric. Separation chamber 6 comprises a first, acute-angled, funnel-like extension 9 protruding outwardly from its outer edge 7 for helping drain a content of the separation chamber 6 into satellite bag 5. Separation chamber 6 also comprises a second, obtuse-angled, funnel-like extension 10 protruding from inner edge 8, towards the center of bag 1, for helping funnel separated components into first, second and third satellite bags 2, 3, 4. This bag set can also be used to collect a mononuclear component into satellite bag 2 if a mononuclear component is desired along with a platelet collection.

Separation bag 1 further comprises a semi-flexible disk-shaped connecting element 11 that is connected to inner edge 8 of annular chamber 6. Disk-shaped connecting element 11 comprises three rounded recesses 12 on its inner edge facing second funnel-like extension 10, for partially surrounding three pinch valve members of a rotor of a centrifuge to be described later (diagrammatically shown in doted line in FIG. 2). Disk-shaped connecting element 11 comprises a series of holes 13 for connecting separation bag 1 to the rotor of a centrifuge.

Satellite bag 2 is a whole blood collection bag. Satellite bag 2 is intended for initially receiving a volume of whole blood or composite liquid from a donor (usually about 450 ml) before the separation process. Satellite bag 2 is flat, substantially rectangular, and comprises two reinforced ears at its upper corners having holes 14 for hanging the bag. It is connected to separation bag 1 by transfer tube or tubing or conduit 20 having a first end connected to the upper edge of satellite bag 2 and a second end connected to the second funnel-like extension 10, close to inner circular edge 8. Satellite bag 2 contains a volume of anti-coagulant solution (typically about 63 ml of a solution of citrate phosphate dextrose for a blood donation of about 450 ml). A frangible connector 21 mounted on transfer tube 20 blocks a liquid flow through transfer tube 20 and prevents the anti-coagulant solution from flowing from satellite bag 2 into separation bag 1.

The bag set further comprises a collection tube or tubing or conduit 22 that is connected at one end to the upper edge of satellite bag 2 and comprises, at the other end, a needle protected by a sheath 23. Collection tube 22 is fitted with a clamp 24.

Satellite bag 3 is intended for receiving a plasma component. Satellite bag 3 is flat, substantially rectangular, and comprises two reinforced ears at its upper corners having holes 14 for hanging the bag. It is connected by transfer tube or tubing or conduit 25 to separation bag 1. Transfer tube 25 has a first end connected to the upper edge of satellite bag 3 and a second end connected to the second funnel-like extension 10, close to inner circular edge 8, opposite the second end of the first transfer tube 20 with respect to the tip of the second funnel-like extension 10.

Satellite bag 4 is intended for receiving a platelet component. Alternatively, it can receive a buffy coat component as described below. It is flat, substantially rectangular, and comprises two reinforced ears at its upper corners having holes 14 for hanging the bag. It is connected by transfer tube or tubing or conduit 26 to the separation bag 1. Transfer tube 26 has a first end connected to the upper edge of satellite bag 4 and a second end connected to the tip of the second funnel-like extension 10.

Satellite bag 5 is intended for receiving a red blood cell component. It is flat, substantially rectangular, and comprises two reinforced ears at its upper corners having holes 14 for hanging the bag. It is connected by transfer tube or tubing or conduit 27 to separation bag 1. Transfer tube 27 has a first end connected to the upper edge of satellite bag 5 and a second end connected to the tip of the first funnel-like extension 9. It comprises two tube segments respectively connected to the inlet and the outlet of a leuko-reduction filter 28. The tube segment connected to separation bag 1 is fitted with a clamp 24. The tube segment connected to satellite bag 5 is fitted with a frangible connector 29, which, when broken, allows a flow of liquid between separation bag 1 and satellite bag 5. The filter may be, for example, a filter of the type RCM1 manufactured by Pall Corporation. Such a filter comprises a disk-shaped casing to which radial inlet and outlet ports are connected, in diametrical opposition. The casing, which is made of polycarbonate (GE Lexan HF 1140), has an internal volume of about 18 ml. It is filled with a filtering medium composed of multiple layers of a non-woven web of polyester fibers (about two micron diameter). It is understood, however, that other filters by other manufacturers can also be used. Satellite bag 5 contains a volume of storage solution for red blood cells.

It is understood that the component collected, such as a platelet component, can be collected in bag 3 rather than 4.

Figure 3:
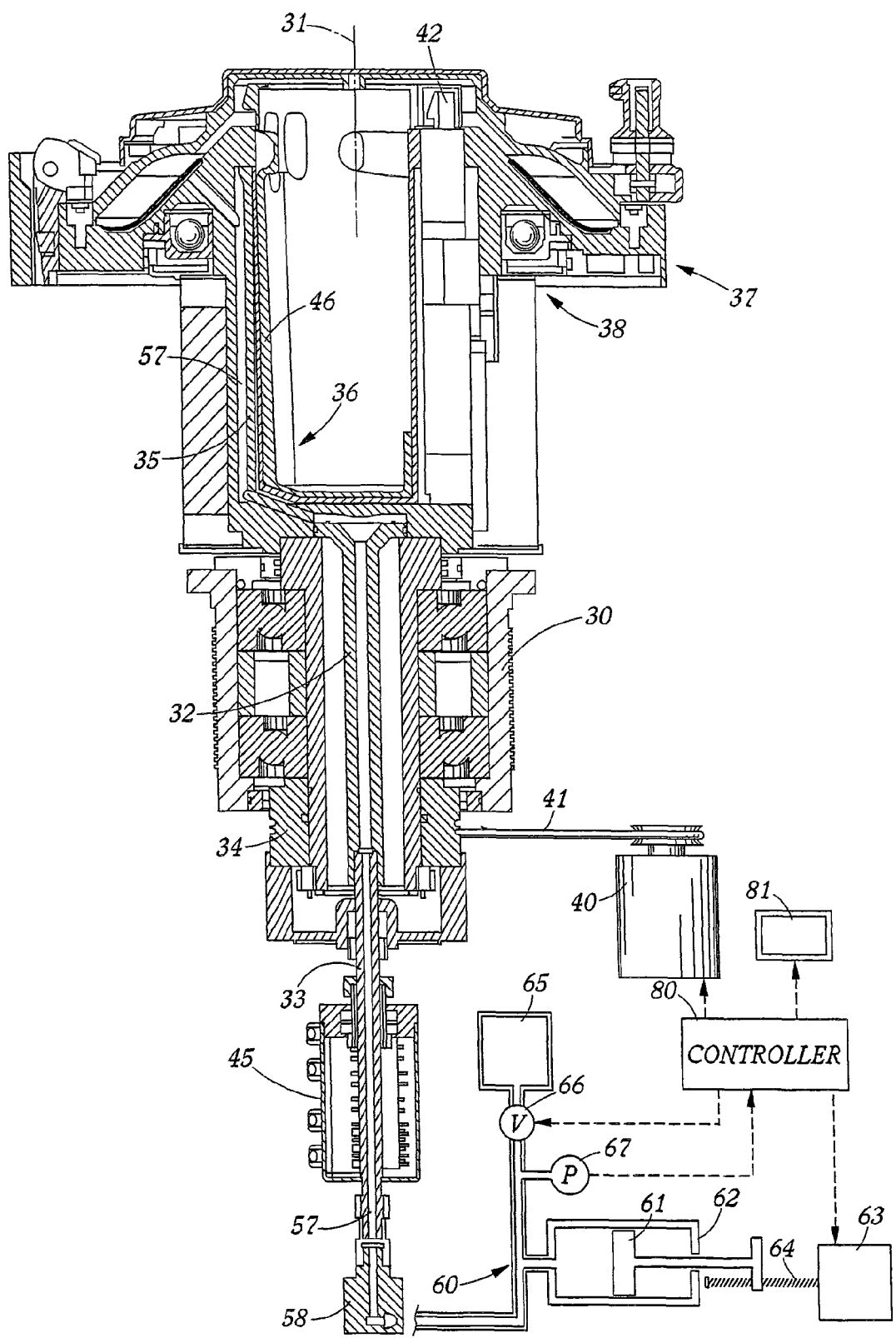
FIG. 3 is a schematic view, partly in cross-section, of a separation apparatus according to the invention.
Figure 4:
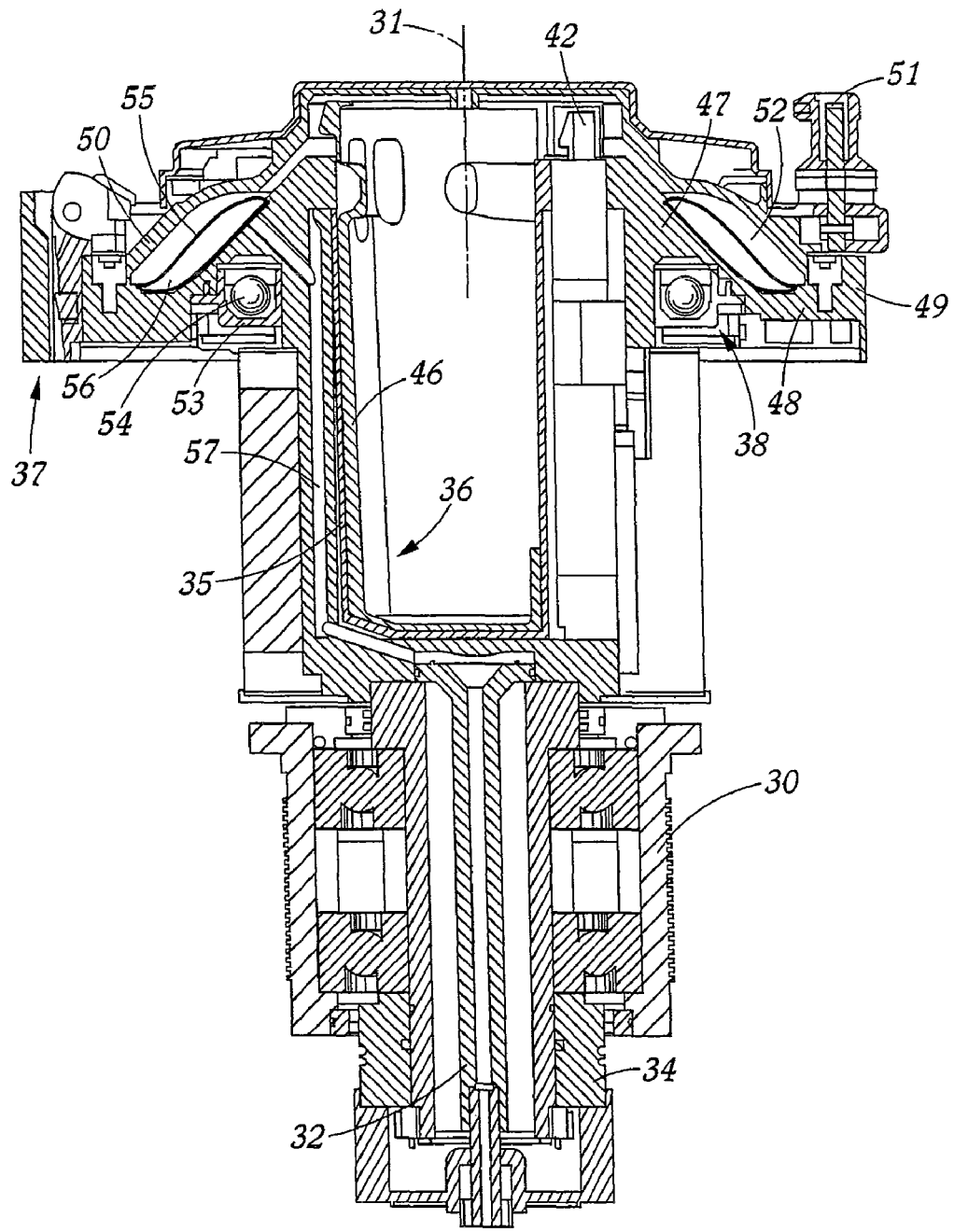
FIG. 4 is a cross-section view of the rotor of a separation apparatus according to the invention.

FIGS. 3 and 4 illustrate an embodiment of an apparatus for separating a volume of composite liquid by centrifugation. The apparatus comprises a centrifuge adapted for receiving the set of separation bags shown in FIGS. 1 and 2, and a component transferring system for causing the transfer of separated components into the satellite bags.

The centrifuge comprises a rotor that is supported by a bearing assembly 30 allowing the rotor to rotate about a vertical central axis 31. The rotor comprises a cylindrical rotor shaft comprising a first upper portion 32 and a second lower portion 33; the upper portion 32 of the shaft extends in part through the bearing assembly 30; a pulley 34 is connected to the lower end of the upper portion 32 of the shaft; a central compartment 35 for containing satellite bags, which is connected to the rotor shaft 32, 33 at the upper end thereof; a support member 36 fitting within the central compartment 35, for supporting at least one satellite bag in a determined position within the central compartment 35; a circular turntable 37 for supporting a separation bag, which is connected to the compartment 35 at the upper end thereof, the central axes of the rotor shaft 32, 33, the compartment 35 and the turntable 37 coinciding with the rotation axis 31; and a balancing assembly 38, which is secured to the turntable 37.

The centrifuge further comprises a motor 40 coupled to the rotor by a belt 41 engaged in a groove of the pulley 34 so as to rotate the rotor about the central vertical axis 31.

The separation apparatus further comprises pinch valve members 42, 43, 44, (see FIG. 2), that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of transfer tubes 20, 25, 26 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. Pinch valve members 42, 43, 44 are mounted at the periphery of central compartment 35 so that their longitudinal axes are coplanar, and parallel to central axis 31 of the rotor, and their heads protrude above the rim of central compartment 35. The position of pinch valve members 42, 43, 44 with respect to separation bag 1 and transfer tubes 20, 25, 26 connected thereto when separation bag 1 is mounted on turntable 37 is shown in doted lines in FIG. 2. Electric power is supplied to pinch valve members 42, 43, 44 through a slip ring array 45 that is mounted around the lower portion 33 of the rotor shaft.

Support member 36 generally comprises a portion of wall 46 that is tilted with respect to the rotation axis 31 of the rotor. A satellite bag secured by an upper portion thereof to an upper part of the tilted wall 46 is pressed against the tilted wall 46 by centrifugation forces during rotation of the rotor and a lower portion of the satellite bag is closer to the axis of rotation than an upper portion thereof. As a result, liquid contained in the supported satellite bag drains, under centrifugation forces, from the supported satellite bag into the separation bag.

Turntable 37 comprises a central frusto-conical portion 47, (see FIG. 4), the upper, smaller edge of which is connected to the rim of compartment 35, an annular flat portion 48 connected to the lower, larger edge of the frusto-conical portion 47, and an outer cylindrical flange 49 extending upwards from the outer periphery of the annular portion 48. Turntable 37 further comprises a vaulted circular lid 50 that is secured to flange 49 by a hinge so as to pivot between an open and a closed position. Lid 50 is fitted with a lock 51 by which it can be locked in the closed position. Lid 50 has an annular interior surface that is so shaped that, when lid 50 is in the closed position, it defines with the frusto-conical portion 47 and the annular flat portion 48 of the turntable 37 a frusto-conical annular compartment 52 having a radial cross-section that has substantially the shape of a parallelogram. The frusto-conical annular compartment 52 (later the "separation compartment"), which has a fixed volume, is intended for containing the separation bag I shown in FIGS. 1 and 2.

Balancing assembly 38, which has generally the shape of a ring, is mounted on the rotor within the space that extends between the upper end of central compartment 35 and the frusto-conical wall 47 of turntable 37. Balancing assembly 38 comprises a ring-shaped housing 53 defining a cavity whose cross-section, along a radial plane, is generally rectangular. The balancing assembly further comprises a plurality of ponderous balls 54 having a diameter that is slightly less than the radial depth of the cavity of housing 53. When the balls 54 are in contact with each other they occupy a sector of housing 52 of about 180 degrees.

The component transferring system comprises a squeezing system for squeezing the separation bag within separation compartment 52 and causing the transfer or expression of separated components into the satellite bags. The squeezing system comprises a flexible annular diaphragm 55 that is so shaped as to line the frusto-conical portion 47 and the annular flat portion 48 of turntable 37, to which it is secured along its smaller and larger circular edges. The squeezing system further comprises a hydraulic pumping station 60 for pumping a hydraulic liquid in and out of an expandable hydraulic or squeezing chamber 56 defined between flexible diaphragm 55 and turntable 37, via a duct 57 extending through the rotor from the lower end of lower portion 33 of the rotor shaft to turntable 37. Pumping station 60 comprises a piston pump having a piston 61 movable in a hydraulic cylinder 62 fluidly connected via a rotary fluid coupling 58 to rotor duct 57. Piston 61 is actuated by stepper motor 63 that moves lead screw 64 linked to the piston rod. Stepper motor 63 can be controlled by discrete increments or steps, each step corresponding to a fraction of turn of the axle of motor 63, that is also to a small linear displacement of piston 61, that is also to a small determined volume of liquid being pumped in or out of hydraulic chamber 56. Hydraulic cylinder 62 is also connected to a hydraulic liquid reservoir 65 having an access controlled by a valve 66 for selectively allowing the introduction or the withdrawal or the flow of hydraulic liquid into and from a hydraulic circuit including hydraulic cylinder 62, rotor duct 57 and the expandable hydraulic chamber 56. A pressure gauge 67 is connected to the hydraulic circuit for measuring the hydraulic pressure therein.

The separation apparatus further comprises at least three sensors 70, 71, and 73, (see FIG. 2), for detecting characteristics of the separation process occurring within a separation bag 1 when the apparatus operates. It is understood that additional sensors could be provided if desired. The three sensors 70, 71, and 73 are embedded in lid 50 at different distances from the rotation axis 31 of the rotor, a sensor 73 being the closest to the rotation axis 31, a sensor 71 being the farthest to the rotation axis 31 and a sensor 70 occupying an intermediate position. When the lid 50 is closed, the three sensors 70, 71, and 73 face separation bag 1 as shown in FIG. 2. Sensor 70 is embedded in lid 50 so as to be positioned over separation chamber 6 a short distance from the end of tube 25 connected to the second funnel-like extension 10 (plasma outlet). Sensor 70 is able to detect a gas/liquid interface, an interface between plasma and a platelet or buffy coat layer, or an interface between platelets or buffy coat and red blood cells. Sensor 71 (later the "outer sensor") is embedded in lid 50 so as to be positioned over separation chamber 6 at about two third of the width of the separation chamber from the inner edge, and it is offset with respect to the second funnel-like extension 10, while being closer to the end of the second transfer tube 25 than to the respective ends of transfer tubes 20, 26. Outer sensor 71 is able to detect a liquid, e.g., blood. Sensor 73, or the inner sensor, is positioned close to transfer tube 26 (platelet or buffy coat outlet). This sensor is able to detect the leading edge of the platelet or buffy coat layer as compared to the plasma layer and the trailing edge associated with the top of the red blood cell layer. Each sensor 70, 71, and 73 can comprise a photocell including an infra-red LED and a photo-detector. Electric power is supplied to the sensors 70, 71, and 73 through slip ring array 45. The instant invention is described with respect to sensor 73 or the platelet or buffy coat sensor, though it is understood that yields of other components could also be determined using the same or other appropriate sensors.

Any type of known sensor can be used such as an optical sensor that receives reflected or transmitted light or an ultrasonic sensor. The sensor needs to be able to determine the interface between the intermediate component, or the platelets or buffy coat and the red blood cells and to be able to distinguish the blood component of interest. Also, if a single sensor is used, it needs to be able to detect the interface between the plasma and the intermediate component. It is understood though that two sensors could be used, one to detect the leading edge of the intermediate layer and one to detect the trailing edge.

The separation apparatus further comprises a controller 80 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into satellite bags 2, 3, 4. The information relative to the various transfer flow rates can be expressed, for example, as hydraulic liquid flow rates in the hydraulic circuit, or as rotation speeds of stepper motor 63 of hydraulic pumping station 60. The microprocessor is further programmed for receiving, directly or through the memory, information from pressure gauge 67 and from photocells 70, 71, 73 and for controlling centrifuge motor 40, stepper motor 63, and pinch valve members 42, 43, 44 so as to cause the separation apparatus to operate along a selected separation protocol. The microprocessor can further predict a yield based on the sensor 73 signal.

An example of a separation protocol aimed at the preparation of blood components from a whole blood donation, namely a plasma component, a platelet component, and a red blood cell component, is explained below. Alternatively, the protocol can be used for a four component collection with white blood cells also being collected in the whole blood bag 2. Similarly, the protocol can be used for a two component collection with fewer satellite bags. Buffy coat platelets could also be collected instead of the platelet product.

The operation of the separation apparatus is described below.

At the beginning of the process, satellite bag 2 of the bag set of FIG. 1 contains a volume of anti-coagulated whole blood (usually about 500 ml). Collection tube 22 has been sealed and cut close to satellite bag 2. Clamp 24 on transfer tube 27 connecting satellite bag 5 to separation bag 1 is closed. The four satellite bags 2, 3, 4, 5 are superposed one upon another so as to form a stack that is inserted into bag loader 36 so that satellite bag 2 is adjacent the tilted wall 46 of bag loader 36. Satellite bags 2, 3, 4, 5 are secured by their upper ears to an upper part of bag loader 36, above the tilted wall 46. In this position, they are substantially located on one side of a plane containing the rotation axis 31 of the rotor, and a lower portion of satellite bag 2 containing the volume of whole blood is closer to the rotation axis 31 than an upper portion thereof.

Separation bag 1 is then laid on turntable 37 and pins (not shown) protruding on turntable 37 around the opening of central compartment 35 are engaged in holes 13 of the disk-shaped connecting element 11 of separation bag 1. Transfer tube 20 connecting satellite bag 2 to separation bag 1 is engaged in pinch valve member 42, transfer tube 25 connecting satellite bag 3 to separation bag 1 is engaged in pinch valve member 43, and transfer tube 26 connecting satellite bag 4 to separation bag 1 is engaged in pinch valve member 44.

Frangible connector 21, which blocks communication between satellite bag 2 and separation bag 1, is broken. Lid 49 of the rotor is closed.

Next, pinch valve member 42 is opened and pinch valve members 43, 44 are closed. The rotor is set in motion by centrifuge motor 40 and its rotation speed increases steadily until it reaches a first centrifugation speed (e.g. about 1500 RPM). When outer cell 71 detects blood, valve member 43 controlling a flow of fluid through transfer tube 25 connected to satellite bag 3 (in which a plasma component will be later transferred) is opened for a predetermined amount of time (for example, about 30 seconds) so as to allow air to vent from separation bag 1 when blood pours therein.

If outer cell 71 has not detected blood within a predetermined period of time following the start of the centrifugation process, control unit 80 causes the rotor to stop and an alarm to be emitted. This could happen in particular if frangible connector 21 has inadvertently not been broken.

After the whole content of satellite bag 2 has been transferred into separation bag 1, pinch valve member 42 is opened, and pinch valve members 43, 44 are closed. The rotor rotates at the first rotation speed (about 1500 RPM). Pumping station 60 is actuated so as to pump hydraulic liquid at a constant flow rate (for example, about 240 ml/min) into hydraulic chamber 56 and consequently squeeze separation bag 1. The air present in separation bag 1 is expelled into satellite bag 2 that held the whole blood. Alternatively, if plasma is not collected, it can be purged into plasma bag 3. After a predetermined period of time following the detection of an interface air/liquid by sensor 70, the pumping station 60 is stopped and pinch valve member 42 is closed. A small residual volume of air remains in separation bag 1.

The speed of the rotor is increased steadily until it reaches a second, high, centrifugation speed (for example, about 3200 RPM, so-called "hard spin") at which the blood components will sediment at the desired level with plasma being the lighter density component, platelets or buffy coat being the medium density cellular component, and blood cells being the heavier density cellular component.

The rotor is rotated at the second centrifugation speed for a predetermined period of time (for example, about 220 seconds), which is selected so that, whatever the hematocrit of the whole blood initially transferred in the separation chamber 1, the blood sediments therein at the end of the predetermined period to a point where the hematocrit of the outer annular red blood cell layer is about 90 and the inner annular plasma layer is substantially devoid of cells. In more detail, at the outcome of this sedimentation stage, the separation bag 1 exhibits three layers: a first inner layer mainly comprising plasma, a second intermediate layer mainly comprising platelets and possibly some white blood cells and a third outer layer mainly comprising red blood cells, and white blood cells (lymphocytes, monocytes and granulocytes) for a platelet collection. For a buffy coat collection the first inner layer mainly comprises plasma, the second intermediate layer mainly comprises platelets and white blood cells with possibly a small amount of plasma and red blood cells, (the buffy coat). The third outer layer mainly comprises red blood cells.

After a predetermined period of time, pinch valve member 43 controlling access to satellite bag 3 is opened. Pumping station 60 is actuated so as to pump hydraulic liquid at a constant flow rate (for example, about 150-220 ml/min) into hydraulic chamber 56. The expanding hydraulic chamber 56 squeezes separation bag 1 and causes the transfer or expression of plasma into satellite bag 3. The pinch valve member 43 is closed after a predetermined period of time has elapsed following the detection of the inward moving plasma and platelet/mononuclear cell interface by the intermediate sensor 70. At the end of this stage, most of the total volume of plasma is in satellite bag 3.

The transfer flow rate of the plasma component (which is directly related to the flow rate of the hydraulic fluid or liquid) is selected to be as high as possible without disturbing the platelet layer so as to avoid contaminating the plasma component with platelets.

For the platelet collection protocol with platelets as the intermediate layer, only one platelet collection is described. It is also understood that plasma remixing with platelets can occur to maximize platelet collection or to collect platelets with some plasma.

Pinch valve member 44 controlling the access to satellite bag 4 is opened and pinch valve members 42, 43 remain closed. The rotor continues to rotate at 3200 rpm. Pumping station 60 is actuated so as to pump or flow hydraulic liquid at a platelet flow rate into hydraulic chamber 56 and consequently squeeze separation bag 1 and cause the transfer or expression of the platelet component into satellite bag 4. Sensor 73 detects the leading edge of the platelet layer as distinguished from the prior plasma level. The transfer flow rate of the platelet component (which is directly related to the flow rate of the hydraulic fluid) is selected to be high enough for preventing the suspended platelets from sedimentation, without, at the same time, triggering the activation of the platelets.

A predetermined time after sensor 73 detects the trailing edge of the platelet layer or an interface between the suspended platelets and white blood/red blood cells, the pumping station is stopped and pinch valve member 44 is then closed.

If white blood cells are also collected pinch valve 42 is opened and pinch valve members 43 and 44 remain closed. Pumping station 60 is actuated to pump hydraulic liquid at a white blood cell flow rate into hydraulic chamber 56 to squeeze bag 1 and express or cause the transfer of the white blood cells into bag 2. It is also understood that red blood cells can alternatively be collected by expression or squeezing with hydraulic liquid.

After final expression of the desired components the rotation speed of the rotor is decreased until the rotor stops, pumping system 60 is actuated and reversed so as to pump the hydraulic liquid from hydraulic chamber 56 at a high flow rate (for example, about 800 ml/min) until hydraulic chamber 56 is substantially empty, and pinch valve members 42, 43, 44 are actuated so as to seal and cut transfer tubes 20, 25, 26. Red blood cells and white blood cells, (if not collected) remain in separation bag 1.

Lid 50 of the rotor is opened and separation bag 1 connected to satellite bag 5 is removed. Clamp 24 on transfer tube 27 is opened. Frangible connector 29 blocking communication between satellite bag 5 and leuko-reduction filter 28 is broken. The storage solution contained in satellite bag 5 is allowed to flow by gravity through filter 28 and into separation bag 1 where it is mixed with the red blood cells so as to lower the viscosity thereof. The content of separation bag 1 is then allowed to flow by gravity drain through filter 28 and into satellite bag 5. The white blood cells (granulocytes and residual monocytes and lymphocytes) are trapped by filter 28, so that the ultimate packed red blood cell component in the bag 5 is substantially devoid of white blood cells. The gravity drain of the separation bag is an alternative to the red blood cells being collected by hydraulic expression.

As previously noted, the invention also includes a buffy coat protocol with buffy coat as the intermediate layer. As described above bag 4 or even bag 3 could be used to collect a buffy coat product for further processing. That is, the buffy coat product could be separated from whole blood and collected using the apparatus and method described above. In the variation wherein a buffy coat product is collected, after plasma collection, pinch valve 44 will open while the rotor continues to rotate at the same rpm for platelet collection. Pumping station 60 is activated to pump the buffy coat at a buffy coat flow rate. The hydraulic fluid squeezes the separation bag to cause the transfer of the buffy coat platelets into satellite bag 4. The sensor 73 detects the leading edge of the buffy coat collection. A predetermined time after the sensor 73 detects the trailing edge or the interface between the white blood cells in the buffy coat and red blood cells, the pumping station is stopped and pinch valve member 44 is closed. The sensor 73 detects the interface between the granulocytes and red blood cells so that the mononuclear cells and granulocytes as well a small amount of red blood cells and plasma will be collected with the platelets to form the buffy coat.

The rotor is then decreased in speed, the pumping station reversed, and the tubes are sealed and cut as described in the platelet collection protocol, The red blood cells and some granulocytes remain in the separation bag. The red blood cells may be optionally filtered as described above.

Figure 5:
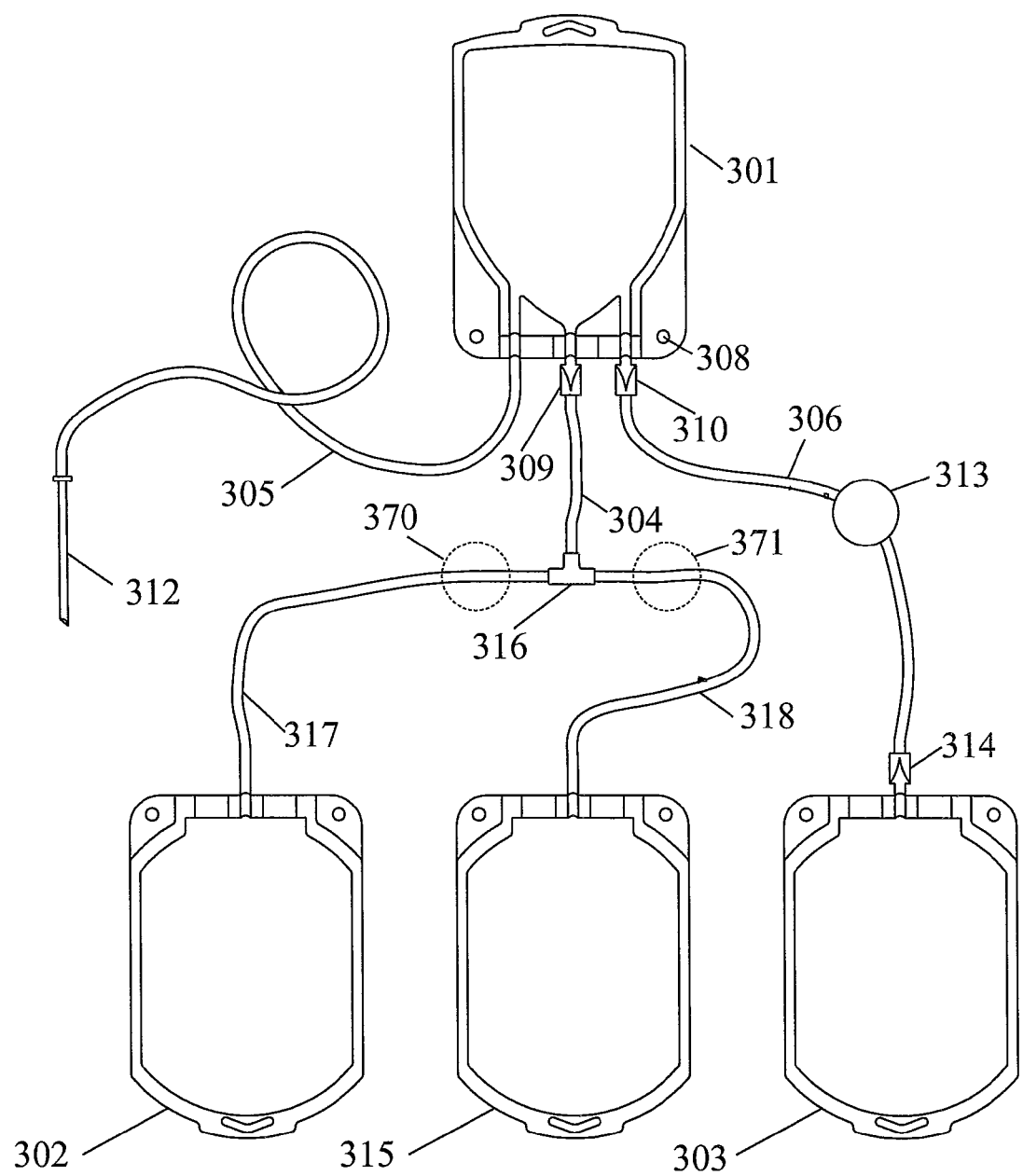
FIG. 5 is a schematic view of a set of bags designed for cooperating with an alternate separation apparatus.

An alternate separation apparatus and method will now be described that is capable of separating multiple bags or containers of composite liquid into components on a single apparatus. FIG. 5 shows an example of a set of bags adapted to the separation of a composite liquid (e.g. whole blood) into a first component (e.g. a plasma component), an intermediate component (e.g. a platelet component or a buffy coat component), and a second component (e.g. a red blood cell component). This bag set comprises a flexible separation bag 301 and three flexible satellite bags 302, 303, 315 connected thereto.

A T-shaped three-way connector 316 is provided having its leg connected by the first tube 304 to the separation bag 301, a first arm connected by a fourth tube 317 to the first satellite bag 302 (plasma component bag), and a second arm connected by a fifth tube 318 to the third satellite bag 315 (platelet component bag). The first and second satellite bags 302, 303, and the third satellite bag 315 are flat and substantially rectangular. The bag 303 may receive a red blood cell component.

Figure 6:
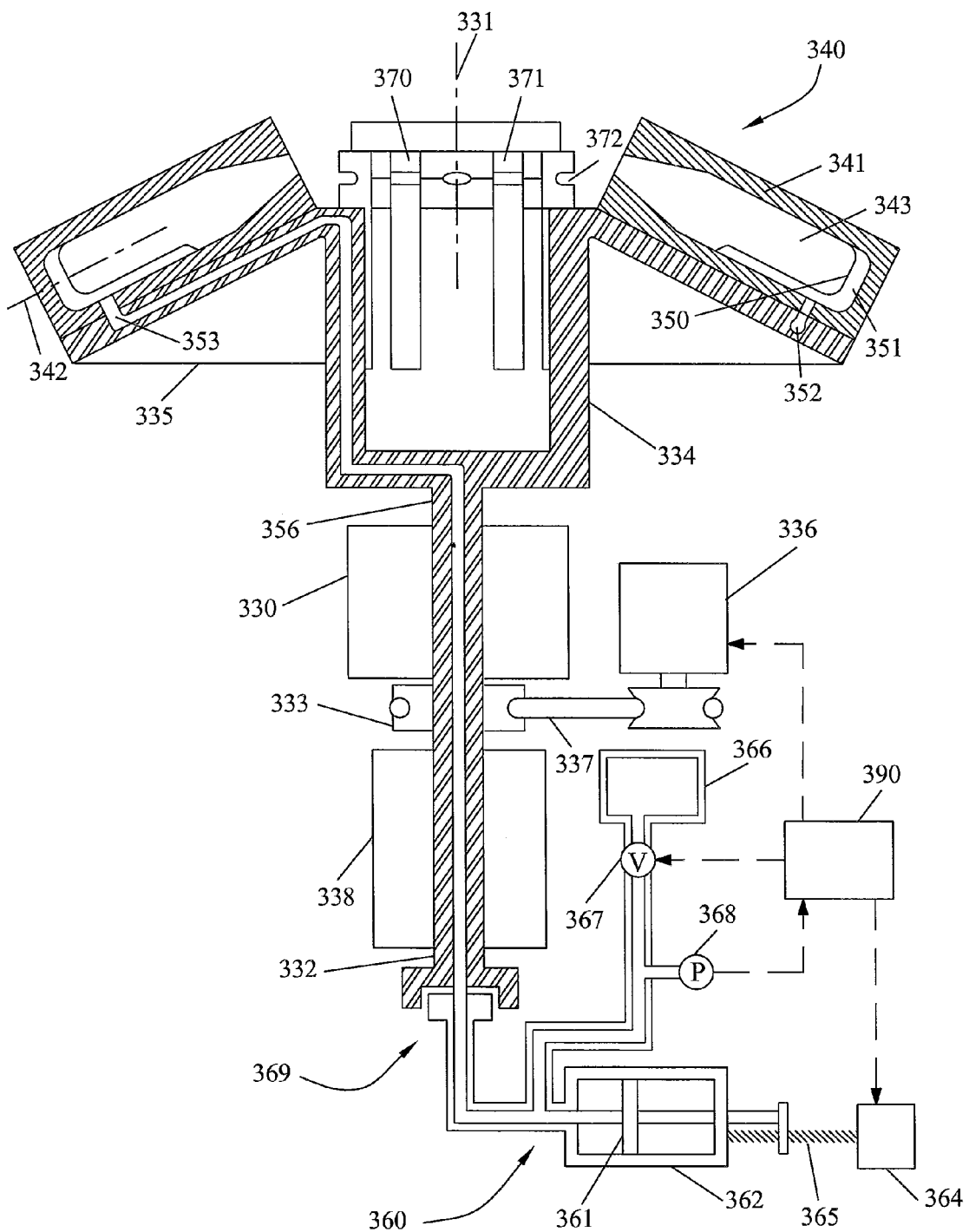
FIG. 6 is a partly in cross-section view of the rotor of the alternate separation apparatus.
Figure 7:
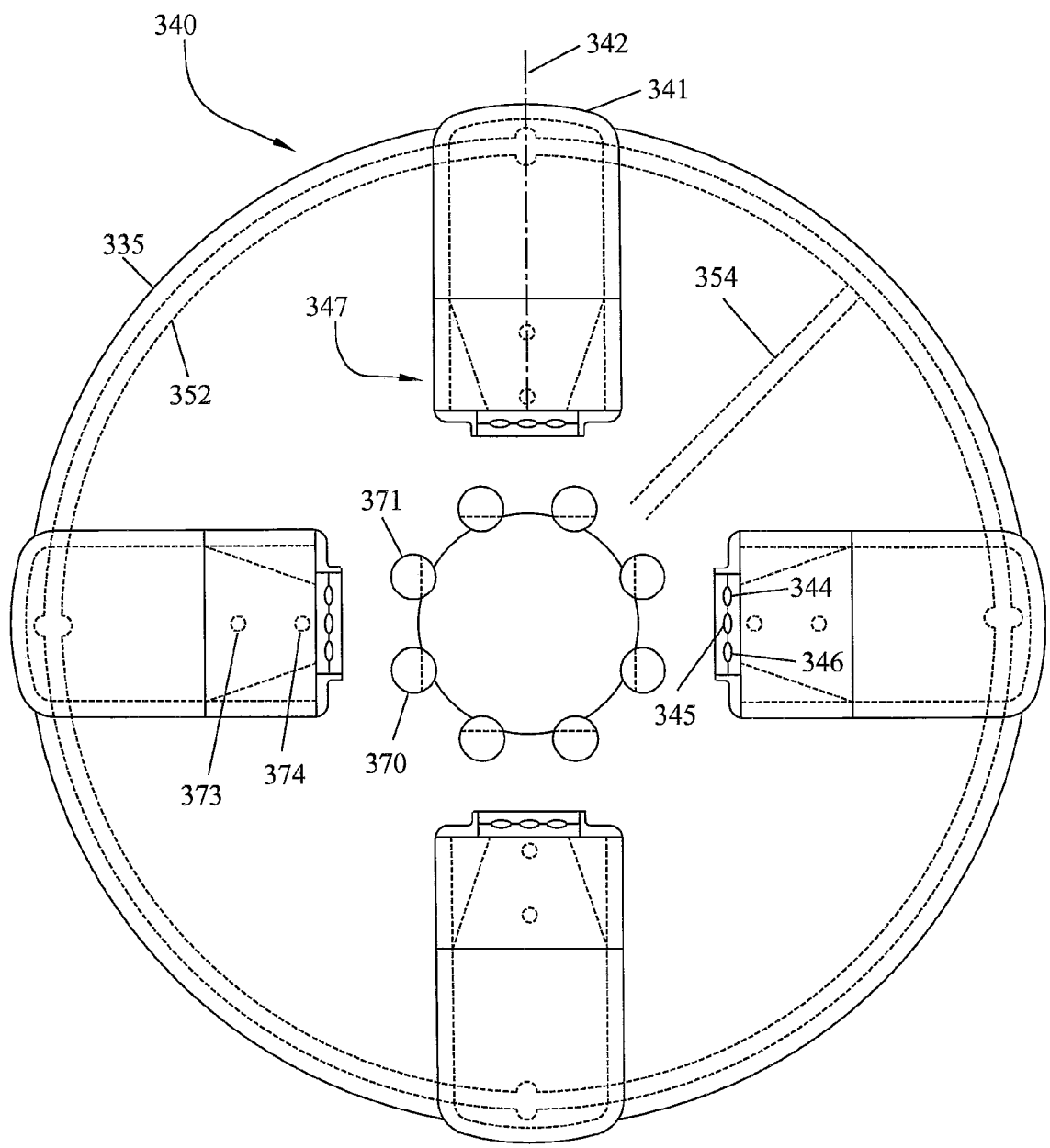
FIG. 7 is a top schematic view of the alternate separation apparatus

FIGS. 6 and 7 show an embodiment of an apparatus for simultaneously separating by centrifugation four discrete volumes of a composite liquid. The apparatus includes: a centrifuge adapted to receive four of the set of bags shown in FIG. 5, with the four discrete volumes of a composite liquid contained in the four separation bags; a component transferring system for transferring at least one separated component from each separation bag into a satellite bag connected thereto; and a balancing system for initially balancing the rotor when the weights of the four separation bags are different.

The centrifuge comprises a rotor that is supported by a bearing assembly 330 allowing the rotor to rotate around a rotation axis 331. The rotor comprises: a cylindrical rotor shaft 332 to which a pulley 333 is connected; a storage device including a central cylindrical container 334 for containing satellite bags, which is connected to the rotor shaft 332 at the upper end thereof so that the longitudinal axis of the rotor shaft 332 and the longitudinal axis of the container 334 coincide with the rotation axis 331, and a frusto-conical turntable 335 connected to the upper part of the central container 334 so that its central axis coincides with the rotation axis 331. The frusto-conical turntable 335 flares underneath the opening of the container 334. Four identical separation cells 340 are mounted on the turntable 335 so as to form a symmetrical arrangement with respect to the rotation axis 331.

The centrifuge further comprises a motor 336 coupled to the rotor by a belt 337 engaged in a groove of the pulley 333 so as to rotate the rotor about the rotation axis 331.

Each separation cell 340 comprises a container 341 having the general shape of a rectangular parallelepiped. The separation cells 340 are mounted on the turntable 335 so that their respective median longitudinal axes 342 intersect the rotation axis 331, so that they are located substantially at the same distance from the rotation axis 331, and so that the angles between their median longitudinal axes 342 are substantially the same (i.e. 90 degrees). The exact position of the separation cells 340 on the turntable 335 is adjusted so that the weight on the turntable is equally distributed when the separation cells 340 are empty, i.e. so that the rotor is balanced. It results from the arrangement of the separating cells 340 on the turntable 335 that the separating cells 340 are inclined with respect to the rotation axis 331 of an acute angle equal to the angle of the frustum of a cone that geometrically defines the turntable 335.

Each container 341 comprises a cavity 343 that is so shaped and dimensioned as to loosely accommodate a separation bag 301 full of liquid, of the type shown in FIG. 5. The cavity 343 (which will be referred to later also as the "separation compartment") is defined by a bottom wall, that is the farthest to the rotation axis 331, a lower wall that is the closest to the turntable 335, an upper wall opposite to the lower wall, and two lateral walls. The cavity 343 comprises a main part, extending from the bottom wall, which has substantially the shape of a rectangular parallelepiped with rounded angles, and an upper part, which has substantially the shape of a prism having convergent triangular bases. In other words, the upper part of the cavity 343 is defined by two couples of opposite walls converging towards the central median axis 342 of the cavity 343. One interest of this design is to cause a radial dilatation of the thin layer of a minor component of a composite fluid (e.g. the platelets in whole blood) after separation by centrifugation, and makes it more easily detectable in the upper part of a separation bag. The two couples of opposite walls of the upper part of the separation cell 340 converge towards three cylindrical parallel channels 344, 345, 346, opening at the top of the container 341, and in which, when a separation bag 301 is set in the container 341, the three tubes 304, 305, 306 extend.

The container 341 also may have a hinged lateral lid 347 and a securing system, such as pins, for securing a separation bag 301 within the separation cell 340.

The separation apparatus further comprises a component transferring system for transferring at least one separated component from each separation bag into a satellite bag connected thereto. The component transferring means comprises a squeezing system for squeezing the separation bags 301 within the separation compartments 343 and causing the transfer of separated components into satellite bags 302, 315.

The squeezing system comprises a flexible diaphragm 350 that is secured to each container 341 so as to define an expandable chamber 351 in the cavity thereof. More specifically, the diaphragm 350 is dimensioned so as to line the bottom wall of the cavity 343 and a large portion of the lower wall of the cavity 343, which is the closest to the turntable 335.

The squeezing system further comprises a peripheral circular manifold 352 that forms a ring within the turntable 335 extending close to the periphery of the turntable 335. Each expansion chamber 351 is connected to the manifold 352 by a supply channel 353 that extends through the wall of the respective container 341, close to the bottom thereof.

The squeezing system further comprises a hydraulic pumping station 360 for pumping a hydraulic liquid in and out the expandable chambers 351 within the separation cells 340. The hydraulic liquid is selected so as to have a density slightly higher than the density of the more dense of the components in the composite liquid to be separated (e.g. the red blood cells, when the composite liquid is blood). As a result, during centrifugation, the hydraulic liquid within the expandable chambers 351, whatever the volume thereof, will generally remain in the most external part of the separation cells 340. The pumping station 360 is connected to the expandable chambers 351, through a rotary seal 369, by a duct 356 that extends through the rotor shaft 332, the bottom and lateral wall of the central container 334, and, from the rim of the central container 334, radially through the turntable 335 where it connects to the manifold 352.

The pumping station 360 comprises a piston pump having a piston 361 movable in a hydraulic cylinder 362 fluidly connected via a rotary fluid coupling 363 to the rotor duct 356. The piston 361 is actuated by a stepper motor 364 that moves a lead screw 365 linked to the piston rod. The hydraulic cylinder 362 is also connected to a hydraulic liquid reservoir 366 having an access controlled by a valve 367 for selectively allowing the introduction or the withdrawal of hydraulic liquid into and from a hydraulic circuit including the hydraulic cylinder 362, the rotor duct 356 and the expandable hydraulic chambers 351. A pressure gauge 368 is connected to the hydraulic circuit for measuring the hydraulic pressure therein.

The separation apparatus further comprises four pairs of a first and second pinch valve members 370, 371 that are mounted on the rotor around the opening of the central container 334. Each pair of pinch valve members 370, 371 faces one separation cell 340, with which it is associated. The pinch valve members 370, 371 are designed for selectively blocking or allowing a flow of liquid through a flexible plastic tube, and selectively sealing and cutting a plastic tube. Each pinch valve member 370, 371 comprises an elongated cylindrical body and a head having a groove 372 that is defined by a stationary upper jaw and a lower jaw movable between an open and a closed position. The groove 372 is so dimensioned that one of the tubes 304, 317, 318 of the bag sets shown in FIG. 5 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 370, 371 are mounted inside the central container 334, adjacent the interior surface thereof, so that their longitudinal axes are parallel to the rotation axis 331 and their heads protrude above the rim of the container 334. The position of a pair of pinch valve members 370, 371 with respect to a separation bag 301 and the tubes 304, 317, 318 connected thereto when the separation bag 301 rests in the separation cell 340 associated with this pair of pinch valve members 370, 371 is shown in doted lines in FIG. 5. Electric power is supplied to the pinch valve members 370, 371 through a slip ring array 338 that is mounted around a lower portion of the rotor shaft 332.

The separation apparatus further comprises four pairs of sensors 373, 374 for monitoring the separation of the various components occurring within each separation bag when the apparatus operates. Each pair of sensors 373, 374 is embedded in the lid 347 of the container 341 of each separation cell 340 along the median longitudinal axis 342 of the container 341, a first sensor 373 being located the farthest and a second sensor 374 being located the closest to the rotation axis 331. When a separation bag 301 rests in the container 341 and the lid 347 is closed, the first sensor 373 (later the bag sensor) faces the upper triangular part of the separation bag 301 and the second sensor 374 (later the tube sensor) faces the proximal end of the first tube 304. The bag sensor 373 is able to detect blood cells in a liquid. The tube sensor 374 is able to detect the presence of absence of liquid in the tube 304 as well as to detect blood cells in a liquid. It also is able to distinguish the interface or leading edge between plasma and platelets or buffy coat as well as the interface or trailing edge between platelets and buffy coat and red blood cells. Each sensor 373, 374 may comprise a photocell including an infrared LED and a photo-detector. Electric power is supplied to the sensors 373, 374 through the slip ring array 338 that is mounted around the lower portion of the rotor shaft 332.

The separation apparatus further comprises a balancing system for initially balancing the rotor when the weights of the four separation bags 301 contained in the separation cells 340 are different. The balancing system substantially comprises the same structural elements as the elements of the component transferring system described above, namely: four expandable hydraulic chambers 351 interconnected by a peripheral circular manifold 352, and a hydraulic liquid pumping station 360 for pumping hydraulic liquid into the hydraulic chambers 351 through a rotor duct 356, which is connected to the circular manifold 352. In order to initially balance the rotor, whose four separation cells 340 contain four discrete volumes of a composite liquid that may not have the same weight (because the four volumes may be not equal, and/or the density of the liquid may slightly differ from one volume to the other one), the pumping station 360 is controlled so as to pump into the interconnected hydraulic chambers 351, at the onset of a separation process, a predetermined volume of hydraulic liquid that is so selected as to balance the rotor in the most unbalanced situation. For whole blood, the determination of this balancing volume takes into account the maximum difference in volume between two blood donations, and the maximum difference in hematocrit (i.e. in density) between two blood donations. Under centrifugation forces, the hydraulic liquid will distribute unevenly in the four separation cells 340 depending on the difference in weight of the separation bags 301, and balance the rotor. In order to get an optimal initial balancing, the volume of the cavity 343 of the separation cells 340 should be selected so that the cavities 343, whatever the volume of the separation bags 301 contained therein, are not full after the determined amount of hydraulic liquid has been pumped into the interconnected expansion chambers 351. Although hydraulic balancing is shown, it is also noted that separation apparatus may alternately have a balance ring such as shown at 38 in FIGS. 3 and 4.

The separation apparatus further comprises a controller 390 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. The microprocessor is programmed for receiving information relative to sensors including sensor 374 and for controlling the centrifuge motor 336, the stepper motor 364 of the pumping station 360, and the four pairs of pinch valve members 370, 371 so as to cause the separation apparatus to operate along a selected separation protocol. The controller can also predict the yield of a component from its movement with respect to sensor 374.

One option to note with respect to the sensors is that the second sensors 374 can be embedded in the lids 347 of the containers 341 so as to face an upper part of a separation bag 301 close to the connection thereof to the first tube 304 rather than facing the tube itself.

The operation of the separation apparatus of FIGS. 5, 6 and 7 will be described now.

According to a first separation protocol, four discrete volumes of blood are separated into a plasma component, a first cell component comprising platelets, white blood cells, some red blood cells and a small volume of plasma (later the "buffy coat" component) and a second cell component mainly comprising red blood cells. Each volume of blood is contained in a separation bag 301 of a bag set represented in FIG. 5, in which it has previously been collected from a donor using the collection tube 305. After the blood collection, the collection tube 305 has been sealed and cut close to the separation bag.

Four separation bags 301 are loaded into the four separation cells 340. The lids 347 are closed and locked.

The tubes 317 connecting the separation bags 301 to the plasma component bags 302, through the T connectors 316, are inserted in the groove 372 of the first pinch valve members 370. The tubes 318 connecting the separation bags 301 to the buffy coat component bags 315, through the T connector 316, are inserted in the groove 372 of the second pinch valve members 371. The four plasma component bags 302, the four buffy coat component bags 315, the four red blood cell component bags 303 and the four leuko-reduction filters 313 are inserted in the central compartment 334 of the rotor. The pinch valve members 370, 371 are closed and the breakable stoppers 309 in the tubes 304 connecting the separation bags 301 to the T connectors 316 are manually broken.

All the pinch valve members 370, 371 are closed. The rotor is set in motion by the centrifuge motor 336 and its rotation speed increases steadily until it rotates at a first centrifugation speed. The pumping station 360 is actuated so as to pump a predetermined overall volume of hydraulic liquid into the four hydraulic chambers 351, at a constant flow rate. This overall volume of liquid is predetermined taking into account the maximum variation of weight between blood donations, so that, after the pumping of the hydraulic fluids, the weights in the various separation cells 340 are substantially equal and the rotor is substantially balanced.

After balancing, all pinch valve members 370, 371 are closed. The rotor is rotated at a second centrifugation speed (high sedimentation speed or "hard spin") for a predetermined period of time that is so selected that, whatever the hematocrit of the blood in the separation bags 1, the blood sediments in each of the separation bag 301 at the end of the selected period to a point where the hematocrit of the outer red blood cell layer is about 90 and the inner plasma layer does not substantially contain anymore cells. The platelets and the white blood cells thus form an intermediary layer between the red blood cell layer and the plasma layer.

The rotation speed is then decreased to a third centrifugation speed, the four first pinch valve members 370 controlling access to the plasma component bags 302 are opened, and the pumping station 360 is actuated so as to pump hydraulic liquid at a first constant flow rate into the hydraulic chambers 351 and consequently squeeze the separation bags 301 and cause the transfer of plasma into the plasma component bags 302.

When blood cells are detected by the bag sensor 373 in the separation cell 40 in which this detection occurs first, the pumping station 360 is stopped and the corresponding first pinch valve member 370 is closed, either immediately of after a predetermined amount of time selected in view of the volume of plasma that it is desirable in the buffy coat component to be expressed in a next stage.

In the plasma component transfer process described above, the transfer of the four plasma components starts at the same time, run in part simultaneously and stop independently of each other upon the occurrence of a specific event in each separation bag (detection of blood cells by the bag sensor 373).

The control unit 390 is programmed to start the buffy coat expression after the four first pinch valve members 370 are closed, upon receiving information from the last bag sensor 373 to detect blood cells. The initial flow of buffy coat is detected by the tube sensor 374.

At the onset of this stage, the rotation speed remains the same (third centrifugation speed), a first of the four second pinch valve members 371 controlling access to the buffy coat component bags 315 is opened, and the pumping station 360 is actuated so as to pump hydraulic liquid at a third constant flow rate into the hydraulic chambers 351 and consequently squeeze the separation bag 301 in the separation cell 340 associated with the opened second pinch valve members 371 and cause the transfer of the buffy coat component into the buffy coat component bag 302 connected to this separation bag 301. The leading edge or the interface between plasma and buffy coat is sensed by sensor 374.

After a predetermined period of time after red blood cells or the trailing edge is detected by the tube sensor 374 in the separation cell 340 associated with the opened second pinch valve member 371, the pumping station 360 is stopped and the second pinch valve member 371 is closed.

The same process is successively carried out to transfer the buffy coat component from the three remaining separation bags 301 into the buffy coat component bag 302 connected thereto.

In the buffy coat component transfer process described above, the transfers of the four buffy coat components are successive, and the order of succession is predetermined. However, each of the second, third and four transfers starts following the occurrence of a specific event at the end of the previous transfer (detection of red blood cells or trailing edge by the tube sensor 374 or closing of the second valve member 371).

The control unit 390 is programmed to stop the centrifugation process after the four (second) pinch valve members 371 are closed, upon receiving information from the last tube sensor 374 to detect red blood cells or the trailing edge.

The rotation speed of the rotor is decreased until the rotor stops, the pumping station 360 is actuated so as to pump the hydraulic liquid from the hydraulic chambers 351 at a high flow rate until the hydraulic chambers 351 are empty, and the first and second pinch valve members 370, 371 are actuated so as to seal and cut the tubes 317, 318. The red blood cells remain in the separation bags 301.

After removal from the separation apparatus the red blood cells may be filtered.

In another separation procedure, four discrete volumes of blood are separated into a plasma component, a platelet component and a red blood cell component.

This process is similar to that described above except a first, larger, portion of plasma is transferred into the plasma bags 302, while a second, smaller, portion of plasma remains in the separation bags 301. However, the expression of plasma from each separation bag 301 into the attached plasma component bag 302 is stopped immediately after detection of blood cells by the corresponding bag sensor 373, so that the volume of plasma remaining in the separation bag 301 is large enough to allow the platelets to be re-suspended therein.

A platelet component is then prepared in the separation bag 301 while the first and second valve members 370, 371 are closed. The rotor is stopped and the pumping station 360 is actuated so as to pump a volume of hydraulic liquid from the hydraulic chambers 351 at a high flow rate. The rotor is then controlled so as to oscillate back and forth around the rotation axis 331 for a determined period of time, at the end of which the cells in the separation bags 301 are substantially suspended in plasma. The rotor is then set in motion again by the centrifuge motor 336 so that its rotation speed increases steadily until it reaches a fourth centrifugation speed (low sedimentation speed or "soft spin"). The rotor is rotated at the fourth rotation speed for a predetermined period of time that is selected so that the blood sediments in the separation bags 301 at the end of the selected period to a point where the separation bags 301 exhibit an outer layer comprising packed red blood cells and an inner annular layer substantially comprising platelets suspended in plasma.

Then a platelet component is transferred into the platelet bags 315 similar to the transfer of the buffy coat. The sensor 374 detects the leading edge of the platelet layer as well as the trailing edge of such layer when red blood cells are detected. The centrifugal process is then concluded as with the buffy coat collection.

With respect to the embodiments above, in the instant invention, the signals from sensor 73 and 374 can be used to predict the platelet yield in the platelet component or in the buffy coat component. This yield can be determined by using the initial sensor signals (73, 374) indicating cells as compared to plasma to determine the leading edge of the platelet or buffy coat layer. The same sensor 73, 374, can be used to indicate the approach of red blood cells or the trailing edge of the platelet or buffy coat layer. The distance between the signals or between the leading and trailing edge, can be used to estimate the volume flowing pass the sensor 73, 374. Once the volume is known yield can be estimated based on experimental measured yield for similar volumes.

Figure 8:
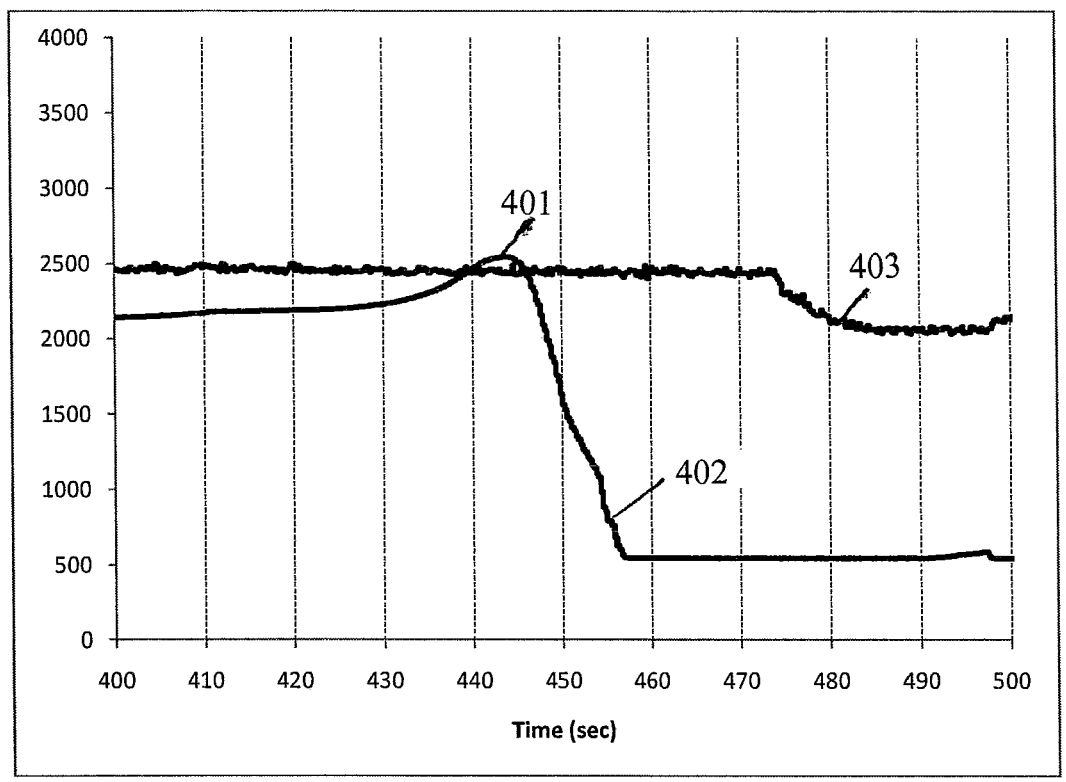
FIG. 8 shows a sensor signal with marked leading and trailing edge.
Figure 9:
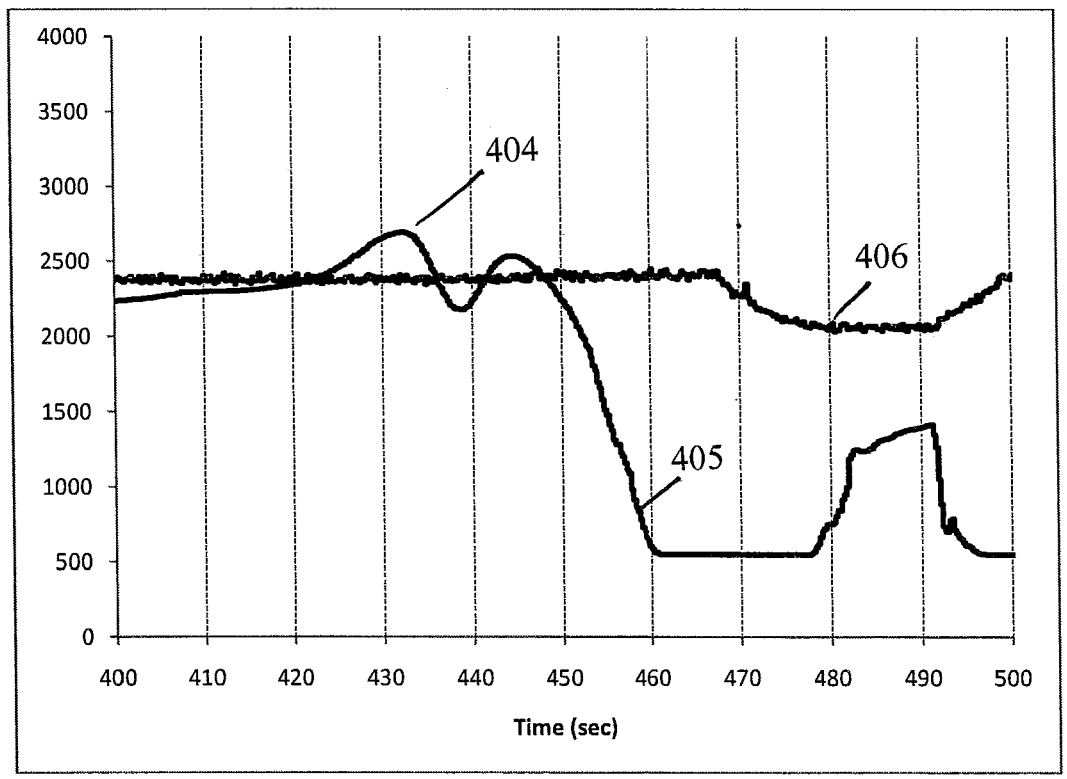
FIG. 9 shows another sensor signal with marked leading and trailing edge.

FIGS. 8 and 9 identify the leading and trailing edges of a photocell such as sensor 73 or 374. In FIG. 8, the photocell or sensor signal is identified as 410. The signal is shown with respect to time and centrifuge revolutions per minutes (rpm). The leading edge of the signal is shown at 401, (platelets or buffy coat passing the sensor 73 or 374) and the trailing edge is at 402 indicating the approach of the red blood cell interface.

With respect to FIG. 9, the photocell or sensor signal is shown at 411 with respect to time and rpm. The leading edge is the initial rise at 404 with the trailing edge shown at 405.

In the separation apparatus described, controllers 80 or 390 can determine the volume from the distance between the leading edge 401 and 404 and the trailing edges 402 and 405 respectively. A predetermined correlation between volume and yield which can be based on previous runs and experience gives the yield from the determined volume.

Figure 10:
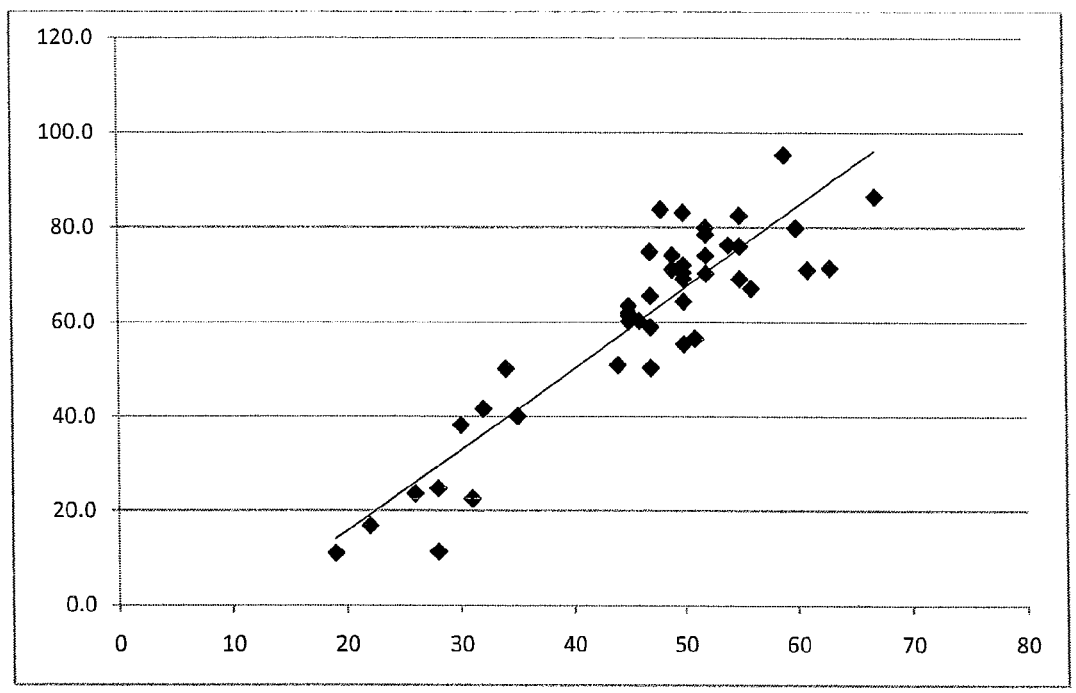
FIG. 10 is a graph comparing measured platelet yield with predicted values.

FIG. 10 illustrates the predicted value (x axis) as a function of volume times 10 expressed past a photocell such as 73, 374 as compared to a measured yield (y axis) using a cell counter.

An alternate prediction method for yield of platelet component can be to integrate the sensor 73 or or 374 signal. Looking at FIG. 11, for example, the circled area essentially represents the platelet or buffy coat expression state or the state when the platelet product or buffy coat product travels under a sensor such as 73 or 374. The x axis indicates the time within the process and the y axis indicates the centrifuge rpm. The area under the curve can be determined by known methods such as by determining the definite integral of the area. Any known method of integrating the signal or determining the area under the curve can be used with one method being in accordance with the trapezoidal rule as shown below. Following this rule the area is equal to the integral form of a real function f(x).

$$\int_{x_1}^{x_2} f(x)dx = \text{Area}$$

$x_1$ and $x_2$ are the end points on the x axis of the area under the curve to be approximated.

The control units 80 or 390 integrates the signal or finds the definite integral of the area under the curve using the above mathematical relationship to determine the predicted platelet yield. It is noted that other area prediction rules such as Simpson's Rule could also be applied.

Figure 11:
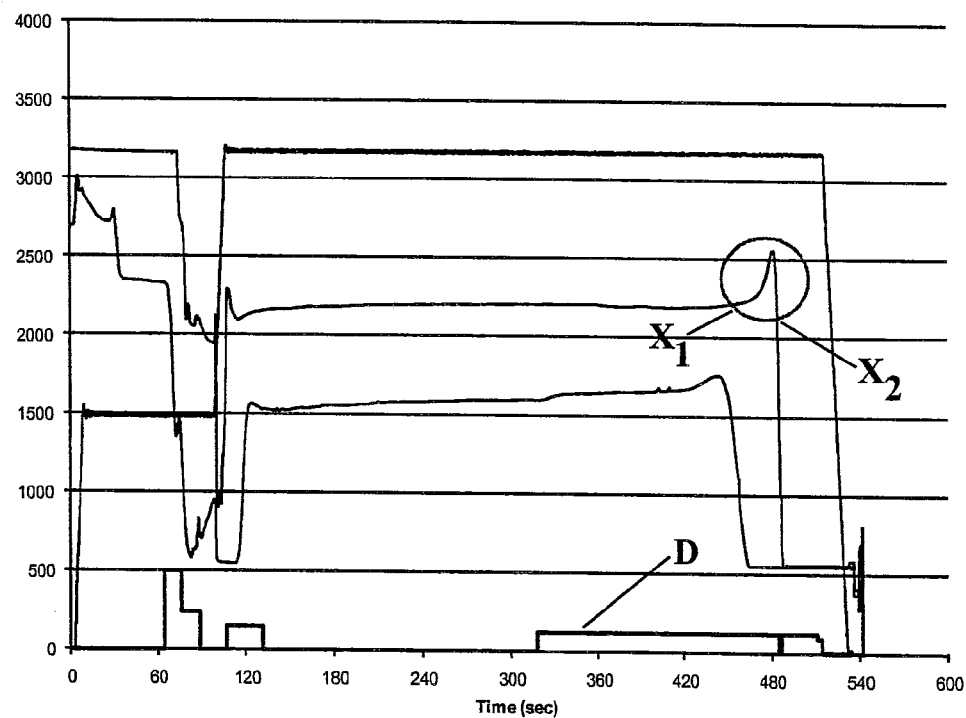
FIG. 11 shows a sensor signal with marked area.

In this example a starting product or composite fluid was separated into a buffy coat collection. The buffy coat collection was at the concentration of 1297E3/μl per the overall volume of starting product or 55 mL. FIG. 11 is a graph of the sensor signal, the hydraulic fluid flow, and the rpm signal plotted versus time. Signal A represents a signal from a photocell such as 70 or 373 that initiates the end of plasma collection after a predetermined time. Signal B represents a signal from a photocell such as 73 or 374 that initiates platelet or buffy coat expression. Signal C is a plot of the rotor rpm. Signal D is a plot of the hydraulic fluid flow. Determining the area under the signal B curve at the spike, as shown in the circle, from the drop in signal A, ($x_1$), to the drop in signal B, ($x_2$), provides a predicted platelet amount for the collected intermediate layer of platelets in the buffy coat. In this example, determining the definite integral yields a predicted amount is 71.3E9 platelets.

The instant invention provides a method for transferring components through the use of a squeezing system including the expression of the components with hydraulic fluid. The prediction method uses a photocell signal to indicate the leading and trailing edges of the cells of interest to determine the volume of such cells. From the volume the yield is predicted. The instant invention uses a single photocell to represent platelet movement and collection. The photocell should be of the known type to be able to distinguish cellular material or components by reflection or transmission or other methods.

It is understood that the same technique can be used for other components to predict their yield from the sensor signal representative of the movement of the component of interest.

Although a single photocell is discussed with respect to the apparatus and method of the instant invention, it is recognized that yield can be predicted from movement detection, and thus volume determination, by other methods following the teachings of the instant invention.

For example, an array of photocells may be used to monitor the movement and determine the leading or trailing edge. Also, even without an array, a different photocell or sensor can be used to detect either the leading or trailing edge. That is, one photocell can be used to detect the leading edge with another detecting the trailing edge. Alternatively, a camera and strobe may be used for the interface detection of one layer or volume of cells from another.

This technique can be used for predicting the yield of the component moving pass the photocell as well as the yield of any component remaining in the separation container or vessel. For example, the starting volume can be determined by introduction of the composite fluid into the separation vessel and the movement of the overall composite fluid with respect to a sensor as well as other methods for determining volume. Similarly, the volume of expressed components can be determined as described above based on movement pass a sensor. The volume of the residual remaining product can be determined by subtracting the expressed volume from the overall composite liquid volume. From such volume the component yield can be predicted.

The technique of the instant invention can also be used to emphasize or select the collection of other components over the collection of a platelet product or a buffy coat product. The collection procedure can thus be changed after initiation. If the platelet collection or buffy coat collection is estimated to be poor the operator can direct the machine performing a separation process, such as the apparatus described above for separating previously collected whole blood, to abandon such platelet or buffy coat collection or to vary subsequent steps of the process in favor of a red blood cell or larger plasma collection. The ability to make these changes early can result in an overall reduced time for the complete process. Similarly, the machine controller itself can make such adjustment based on the information received from sensor 73 or 374. Such change can be made by changing the interface so that more plasma is collected into the platelet layer to maximize plasma collection. Similarly red blood cell collection can start early to adjust the interface more into the platelet or buffy coat layer so fewer red blood cells are lost. The red blood cells would color what was to be a buffy coat or platelet product and indicate to the operator that the platelet or buffy coat collection had been jumped over or skipped. The controllers 80, 390 can make such adjustments or they can be made by operator input based on the predictions from sensors 73 or 374.

As described above, the method can be used during buffy coat separation. That is, sensors can be used to determine the volume of the platelets in the buffy coat and then platelet yield can be predicted from the volume. This permits buffy coat collections to be more accurately pooled to achieve the optimum platelet dosage. That is, the platelet dosage of each buffy coat collection can be predicted. The appropriate buffy coat collection can be selected for pooling such that the sum of the predicted platelets in the selected buffy coat collections achieve proper platelet dosage amount. Those buffy coat collections that do not have the requisite platelet predictions can be discarded in favor of other buffy coat collections.

The invention will now be described with respect to the pooling of buffy coats.

Figure 12:
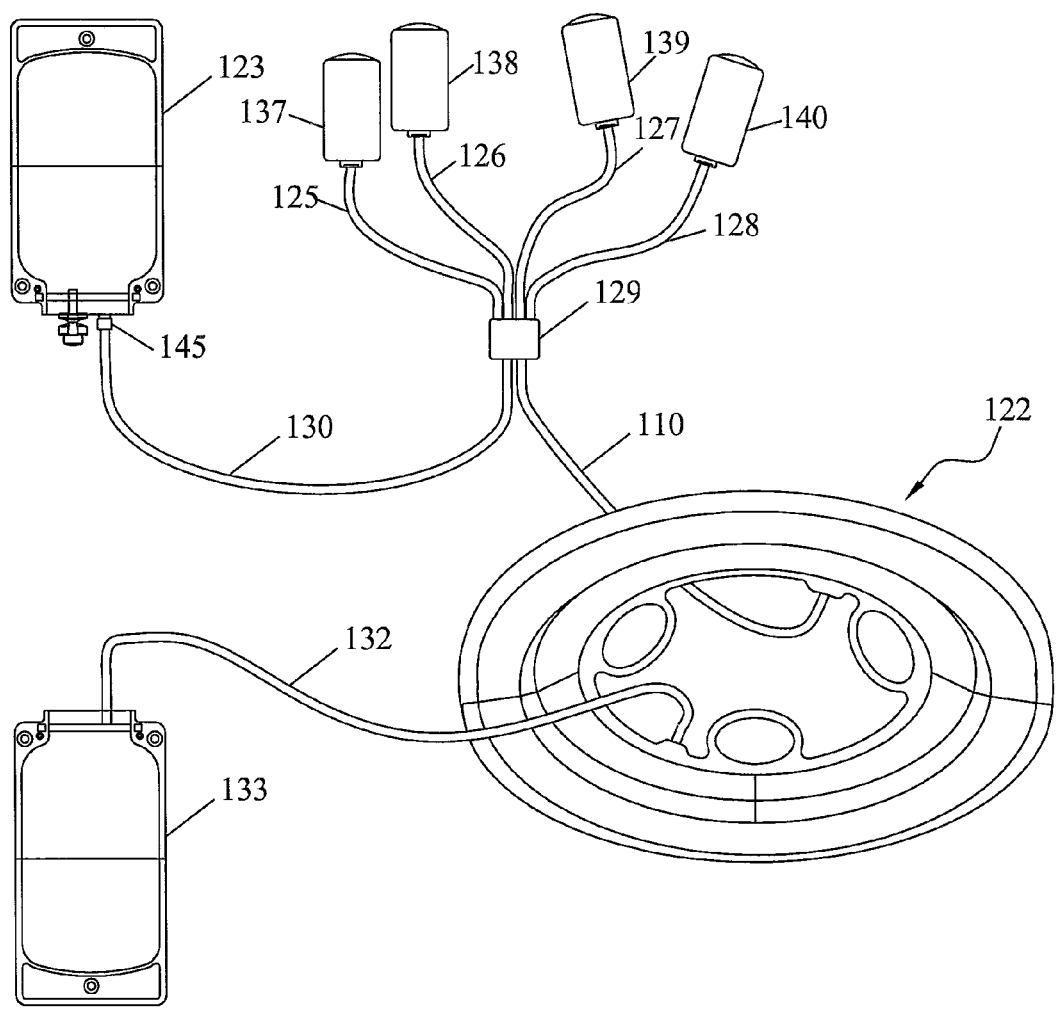
FIG. 12 is a schematic view of a bag set for a centrifuge for producing a platelet product from buffy coats platelets.

FIG. 12 discloses a bag set for buffy coat collection. This bag set comprises an annular flexible bag or separation container 122 for pooling buffy coats and separating platelets contained therein. Buffy coat source bags or containers 137, 138, 139, and 140 are selected based on predicted platelet content in accordance with the method described above, to achieve an estimated desired platelet dosage. After selection, the annular bag 122 is sterilely connected by known methods to flexible buffy coat source bags 137, 138, 139 and 140, through conduits or transfer tubes 125, 126, 127 and 128.

The transfer tubes 125, 126, 127 and 128 are connected by a connector 129 to connect the buffy coat source bags to a source of diluting or washing solution 123 through conduit or transfer tube 130 or to connect the buffy coat source bags to ring bag 122 through conduit or tubing 131. Bag 123 is mounted in a centrifuge, (not shown) to separate the platelets from the white blood cells and any remaining red blood cells in the buffy coat. A valve or frangible connector or other type of clamp is provided at 145 to initially block flow of the diluting or washing solution.

Ring or annular bag 122 is further connected to flexible platelet collection bag or product container 133 through conduit or transfer tube 132.

After the ring bag and the collection bag 133 are placed in or on the rotor of the centrifuge the majority of the contents of the buffy coat bags enter the ring bag 122 through connector 129. Then the diluting fluid from bag 123 flows to the buffy coat source bags 137, 138, 139, and 140 to dilute any remaining product in the bags.

Generally the source bags 137, 138, 139 and 140 are agitated for dilution. After sufficient agitation the diluted remaining buffy coat product flows through connector 129, and transfer tube 131 to ring bag 122.

The process from this point forward becomes similar to a separation process described above. The rotor begins to rotate and increases to 200 rpm to separate the platelet product from any heavier red blood cells. After sedimentation, a transferring or squeezing system presses or expresses the platelet product out of ring bag 122 to the collection bag 133. The transferring system squeezes or expresses the platelet product through transfer tube 132 to platelet collect bag 133.

As a number of buffy coat collections may be discarded by a blood center or blood collection facility, the ability to predict the platelet count in a particular buffy coat collection can facilitate the selection of buffy coat collections for the pooling procedure described above. The selected bags of buffy coat will be used for the 137, 138, 139, and 140 bags in the procedure above.

Figure 13:
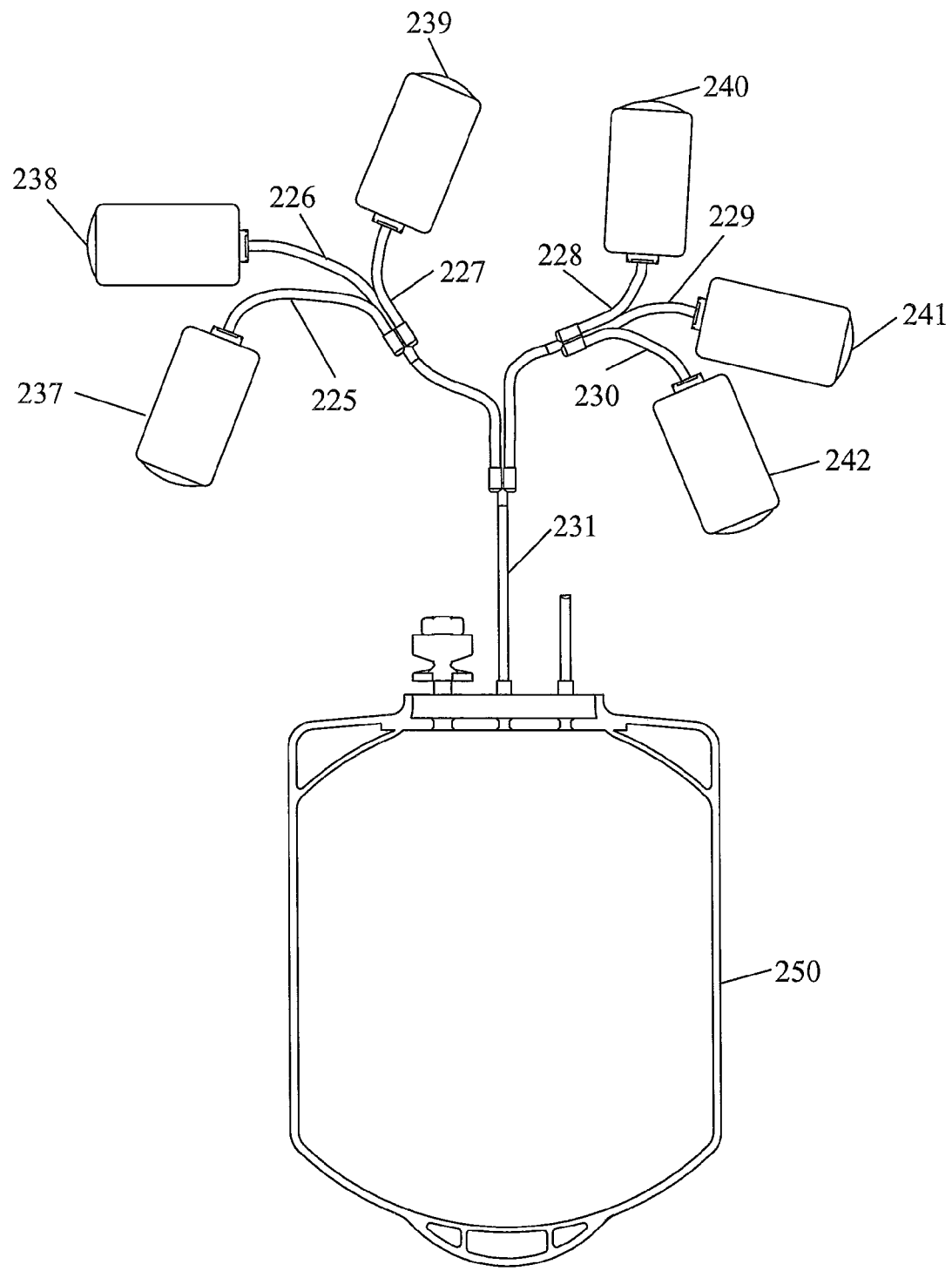
FIG. 13 is a schematic view of a bag set for a centrifuge for producing a platelet product from random donor platelets.

FIG. 13 illustrates a bag set for random donor platelet pooling although it also could be used for buffy coat pooling. This pooling process is very similar except that no further separation is required. The desired random donor platelet collections in bags or containers 237, 238, 239 240, 241 and 242 are sterile docked to the transfer tubes 225, 226, 227, 228, 229 and 230 respectively. These random donor platelet collections are selected based on the predicted platelet content as determined by the method described above. The random donor platelets are then allowed to drain though transfer tube 231 into final collection bag or product container 250. Diluting fluid or platelet storage solution, (not shown), may also be added.

As with the buffy coat collection, the ability to predict the platelet count in a particular random donor platelet product can facilitate the selection of such random donor platelet products for the pooling procedure described above. Thus a blood center can determine which random donor platelet products it may wish to discard and select others such that the sum of the predicted platelet yield in the selected random donor platelet collections approximate the dosage amount of platelets needed.

Figure 14:
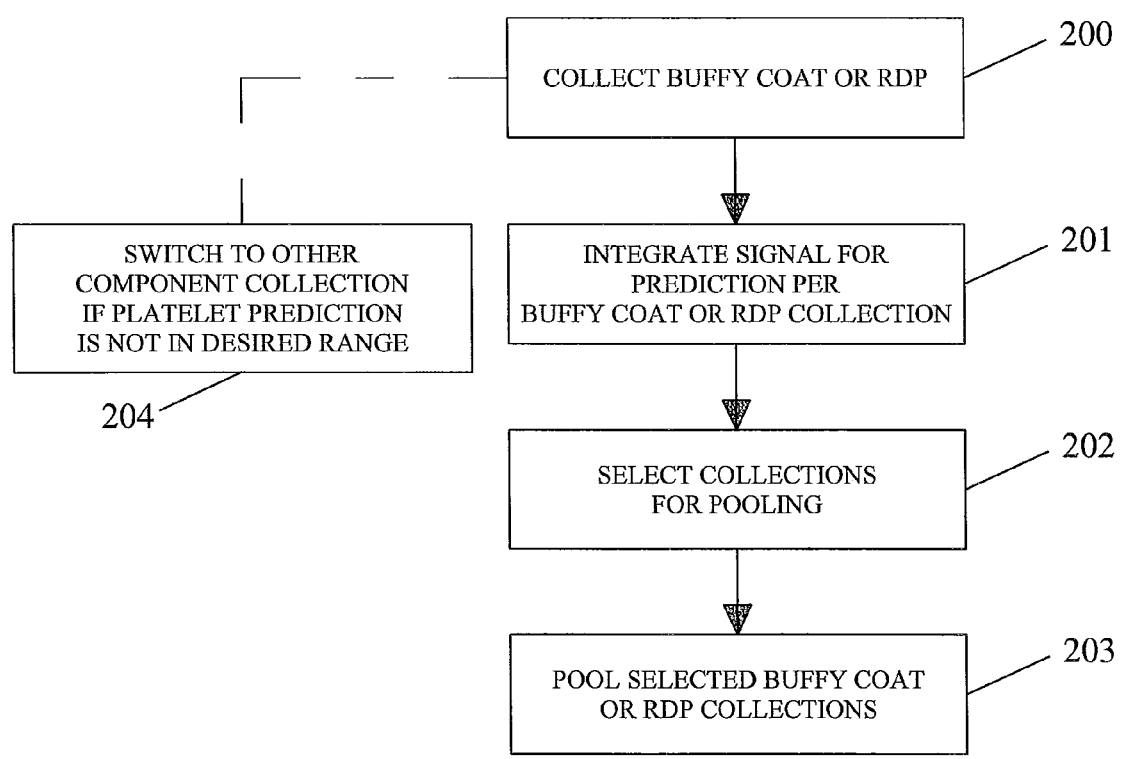
FIG. 14 is a block diagram showing a buffy coat and random donor platelet collection and pooling process with platelet prediction.

FIG. 14 illustrates the buffy coat and random donor platelet, (RDP), procedure, including buffy coat or random donor platelet selection, in block diagram form. As indicated at 200, buffy coats or random donor platelets are collected in a separation apparatus such as that described above. The buffy coat or random donor platelets can be collected in bags 4 or 315 and photocells 73 or 374 can be used to provide a platelet prediction amount for the collection.

Specific buffy coat or random donor platelets collections can then be selected for pooling as indicated at 202 based on their platelet predictions and the known amount needed for a transfusion dose. These will be the buffy coats or random donor platelets utilized for pooling as described in the polling procedures above. Also, those buffy coats or random donor platelet collections with too few platelets may be selected for disposal. The selection process can include a control unit such as 80 or 390 indicating optimum pooling based on inputted platelet prediction amounts. Alternatively, an operator can manually select buffy coat or random donor platelet collections for pooling to achieve the desired dosage or optimum standardization by considering the platelet prediction for each collection.

Apparatus such as that described above in FIG. 12 can be used to pool the buffy coat collections as indicated at 203 to achieve the desired end product or dosage amount. Apparatus such as that described with respect to FIG. 13 can be used to pool the random donor platelets as indicated at 203, to achieve the desired end product or dosage amount.

Alternatively, a buffy coat or random donor platelet collection procedure of the separators described above can be abandoned in favor of an alternative component collection, (such as plasma or red blood cells), if the platelet prediction is not within a desired range as indicated at 204.

Although the prediction technique of the instant invention has been described with respect to platelets and buffy coat it is considered applicable to the collection of other components to provide prediction information for selection of blood products and their usage.

The instant invention is not dependent on a particular pooling apparatus or method. It is understood that the principals of the invention can apply to other cellular separation techniques as well as other pooling techniques.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method of predicting the yield of a selected cellular component
   from a composite blood product comprising
   centrifuging the composite blood product in a separation container to separate the composite blood product into at least the one selected cellular component and another component;
   expressing one of the separated cellular component or the other component from the separation container to a collection container;
   sensing the movement of the expressed component or the other component during the expressing step from the separation container to the collection container to produce a signal indicative of the expressed component; and predicting the yield of the separated cellular component from the signal.

2. The method of claim 1 wherein the expressing step comprises expressing the separated cellular component.

3. The method of claim 2 wherein the sensing step comprises sensing the movement of the separated cellular component with a photocell.

4. The method of claim 3 wherein the sensing step further comprises the photocell sensing the interface between the separated selected cellular component and other cellular components in the composite blood product.

5. The method of claim 2 wherein the separated cellular component comprises buffy coat.

6. The method of claim 5 wherein the composite blood product is whole blood.

7. The method of claim 2 wherein the separated cellular component is a platelet component.

8. The method of claim 7 wherein the centrifuging step further comprises separating a plasma component from the composite blood product; and
expressing the plasma component from the separation container to a plasma collection container prior to expressing the platelet component.

9. The method of claim 7 wherein the composite blood product is whole blood.

10. The method of claim 7 further comprising
determining if the predicted yield is desirable for pooling of the separated platelet component; and
if the predicted yield is not desirable, halting the expressing of the separated platelet component or changing the expressing in favor of the collection of another separated component.

11. The method of claim 2 wherein the predicting step further comprises calculating the area under a portion of the signal representative of the movement of the separated cellular component.

12. The method of claim 11 wherein the calculating step further comprises calculating the definite integral under a portion of the signal curve of the signal.

13. The method of claim 2 wherein the sensing the movement step further comprises determining the volume of the expressed component from the leading edge and trailing edge of the signal.

14. The method of claim 13 wherein the predicting step further comprises predicting the yield from the volume expressed.

15. The method of claim 1 wherein the expressing step comprises expressing the other component.

16. The method of claim 2 wherein the expressing step further comprises squeezing the separation container to express the separated cellular component.

17. The method of claim 16 wherein the squeezing step comprises flowing hydraulic fluid to squeeze the separation container.

18. The method of claim 1 wherein the sensing the movement further comprises determining the volume of the expressed component from the leading edge and trailing edge of the signal.

19. The method of claim 18 wherein the predicting step further comprises predicting the yield from the volume expressed.

20. The method of claim 1 further comprising predicting the yield of a plurality of selected cellular components from a plurality of composite blood products on a centrifuge.

21. Apparatus for predicting the yield of a selected cellular component from a composite blood product comprising
a separation container;
at least one collection container;
a centrifuge for centrifuging the composite blood product in the separation container to separate the composite blood product into a selected cellular component and at least one other component;
a system for expressing one of the separated cellular component or the at least one other component from the separation container to the at least one collection container;
a sensor for sensing the movement of the expressed component during expression from the separation container to the at least one collection container to produce a signal indicative of the expressed component movement; and
a controller for predicting the yield of the expressed component from the signal.

22. The apparatus of claim 21 wherein the system for expressing comprises an hydraulic system for squeezing the separation container to express the expressed component.

23. The apparatus of claim 21 wherein the sensor comprises a photocell.

24. The apparatus of claim 21 wherein the expressed component is the separated cellular component.

25. The apparatus of claim 24 wherein the separated cellular component comprises buffy coat.

26. The apparatus of claim 24 wherein the separated cellular component comprises a platelet component.

27. The apparatus of claim 26 wherein the controller calculates the definite integral under a portion of the signal curve of the signal.

28. The apparatus of claim 26 wherein the composite blood product is whole blood.

29. The apparatus of claim 26 wherein the controller determines if the predicted yield is desirable for pooling of the separated platelet components and if the predicted yield is not desirable, changing the expressing of the separated platelet component in favor of the collection of another separated component.

30. The apparatus of claim 24 wherein the sensor senses the leading edge and the trailing edge of the separated cellular component layer; and
wherein the controller determines the volume of the expressed separated cellular component from the leading and trailing edges.

31. The apparatus of claim 30 wherein the controller predicts the yield of the separated cellular component from the volume.

32. The apparatus of claim 21 wherein the controller calculates the area under a portion of the signal representative of the movement of the expressed component.

33. The apparatus of claim 21 where the composite blood product is whole blood.

34. The apparatus of claim 21 wherein the sensor senses the movement of the other component to determine its volume;
the controller subtracts the volume of the other component from the overall volume of the composite blood product to determine the volume of the selected cellular component; and
the controller predicts the yield of the separated cellular component from its volume.

* * * * *